United States Patent
Egeler et al.

(10) Patent No.: US 10,537,891 B2
(45) Date of Patent: *Jan. 21, 2020

(54) MENISCUS REDUCING MEMBER

(71) Applicant: STEMCELL TECHNOLOGIES INC, Vancouver (CA)

(72) Inventors: Oliver Egeler, North Vancouver (CA); Steven Woodside, Vancouver (CA)

(73) Assignee: STEMCELL TECHNOLOGIES INC., Vancouver (CA)

( * ) Notice: Subject to any disclaimer, the term of this patent is extended or adjusted under 35 U.S.C. 154(b) by 130 days.

This patent is subject to a terminal disclaimer.

(21) Appl. No.: 15/918,798

(22) Filed: Mar. 12, 2018

(65) Prior Publication Data

US 2018/0200711 A1    Jul. 19, 2018

Related U.S. Application Data

(63) Continuation-in-part of application No. 14/760,397, filed as application No. PCT/CA2014/050016 on Jan. 10, 2014, now Pat. No. 9,931,633.

(Continued)

(51) Int. Cl.
*B01L 3/00*    (2006.01)

(52) U.S. Cl.
CPC ....... *B01L 3/508* (2013.01); *B01L 2300/0851* (2013.01); *B01L 2300/0858* (2013.01); *B01L 2300/165* (2013.01); *B01L 2300/166* (2013.01)

(58) Field of Classification Search
CPC ...................................................... B01L 3/508
See application file for complete search history.

(56) References Cited

U.S. PATENT DOCUMENTS

| | | |
|---|---|---|
| 4,122,980 A | 10/1978 | Laverty |
| 4,233,029 A | 11/1980 | Columbus |

(Continued)

FOREIGN PATENT DOCUMENTS

| | | |
|---|---|---|
| CA | 2216378 | 11/1996 |
| CA | 2218378 | 8/1997 |

(Continued)

OTHER PUBLICATIONS

International Preliminary Report on Patentability issued in PCT Application No. PCT/CA2014/050016 dated Jul. 14, 2015.

(Continued)

*Primary Examiner* — Matthew D Krcha
(74) *Attorney, Agent, or Firm* — Bereskin & Parr LLP/S.E.N.C.R.L., S.R.L.

(57) ABSTRACT

A meniscus reducing member for use in a vessel for containing a liquid may include a physical surface feature overlying at least a portion of an interior surface of the vessel. The physical surface feature may have first and second inner surfaces that are generally parallel and at least a third surface extending between the first and second surfaces. The first inner surface, second inner surface and third surfaces may be configured to physically alter a receding contact angle between the liquid and the physical surface feature. A coating material may be applied to at least one of the surfaces of the physical surface feature to chemically alter the receding contact angle between the liquid and the coated surface whereby the receding contact angle formed between the liquid and the meniscus reducing member is between about 90 degrees and less than 180 degrees.

15 Claims, 7 Drawing Sheets

Related U.S. Application Data

(60) Provisional application No. 61/751,012, filed on Jan. 10, 2013.

(56) References Cited

U.S. PATENT DOCUMENTS

| | | | |
|---|---|---|---|
| 4,303,616 | A | 12/1981 | Kano et al. |
| 4,426,451 | A | 1/1984 | Columbus |
| 4,741,619 | A | 5/1988 | Humphries et al. |
| 4,831,224 | A | 5/1989 | Keefer |
| 5,180,555 | A | 1/1993 | Monget |
| 5,540,891 | A | 7/1996 | Portmann et al. |
| 6,074,614 | A | 6/2000 | Hafeman et al. |
| 6,971,530 | B2 | 12/2005 | Darr |
| 6,977,722 | B2 | 12/2005 | Wohlstadter et al. |
| 2003/0228705 | A1 | 12/2003 | Chan et al. |
| 2004/0072367 | A1 | 4/2004 | Ding et al. |
| 2004/0082699 | A1 | 4/2004 | Brown |
| 2005/0047971 | A1 | 3/2005 | Clements et al. |
| 2005/0137355 | A1 | 6/2005 | Buckanin et al. |
| 2005/0170498 | A1 | 8/2005 | Dolley et al. |
| 2005/0226787 | A1 | 10/2005 | Shanler |
| 2005/0244838 | A1 | 11/2005 | Wojtowicz |
| 2006/0123893 | A1 | 6/2006 | Johans et al. |
| 2006/0172412 | A1 | 8/2006 | Perrier et al. |
| 2007/0110907 | A1 | 5/2007 | Brown |
| 2007/0154357 | A1 | 7/2007 | Szlosek |
| 2007/0274871 | A1 | 11/2007 | Jiang |
| 2008/0072964 | A1 | 3/2008 | Kim et al. |
| 2008/0141784 | A1 | 6/2008 | Murakami |
| 2009/0217981 | A1 | 9/2009 | Extrand et al. |
| 2010/0047845 | A1* | 2/2010 | Woodside ............. B01L 3/5085 435/29 |
| 2010/0067105 | A1* | 3/2010 | Egeler .................. B01L 3/5082 359/398 |

FOREIGN PATENT DOCUMENTS

| | | |
|---|---|---|
| CN | 1894351 | 1/2007 |
| EP | 1859866 | 11/2007 |
| JP | 59088084 | 5/1984 |
| JP | 2008035841 | 2/2008 |
| SU | 1455295 | 1/1989 |
| WO | 1996-034697 | 11/1996 |
| WO | 2003050515 | 6/2003 |
| WO | 2005108955 A1 | 11/2005 |
| WO | 2014107811 A1 | 7/2014 |

OTHER PUBLICATIONS

International Search Report issued in corresponding PCT Application No. PCT/CA2014/050016 dated Apr. 29, 2014.

International Preliminary Report on Patentability, dated Aug. 26, 2009 in PCT International Application No. PCT/CA2008/000363.

Schuderer et al., "Effect of the Meniscus at the Solid/Liquid Interface on the SAR Distribution in Petri Dishes and Flasks", Bioelectromagnetics 24, 103-108, 2003.

Supplementary European Search Report dated Nov. 22, 2013 in European Patent Application No. 08714684.

Supplementary European Search Report dated Jul. 15, 2016 in corresponding European Application No. 14737904.4.

Office Action and Search Report dated Apr. 25, 2016 issued in corresponding Chinese Application No. 201480013289.9 (Chinese language and English translation).

Office Action dated Jun. 23, 2017 issued in corresponding Chinese Application No. 201480013289.9 (Chinese language).

Office Action dated Dec. 29, 2016 issued in corresponding Chinese Application No. 201480013289.9 (Chinese and English language).

\* cited by examiner

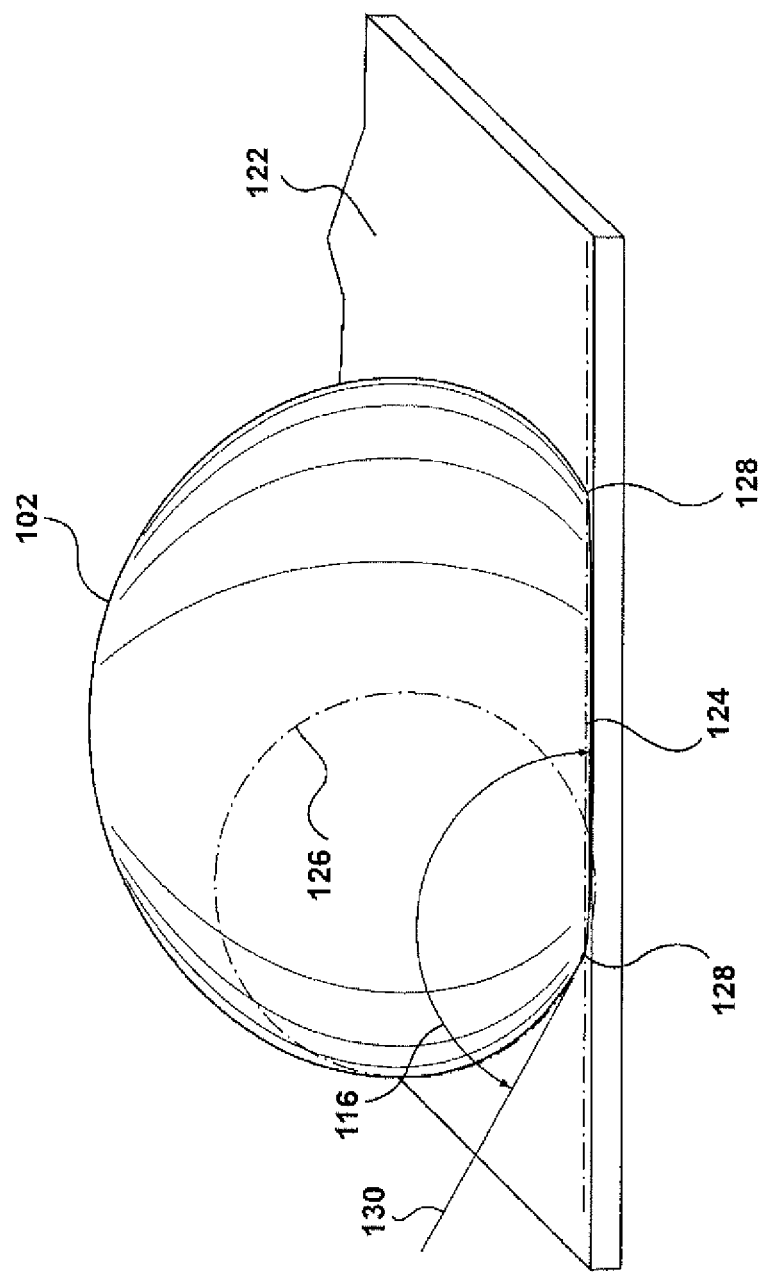

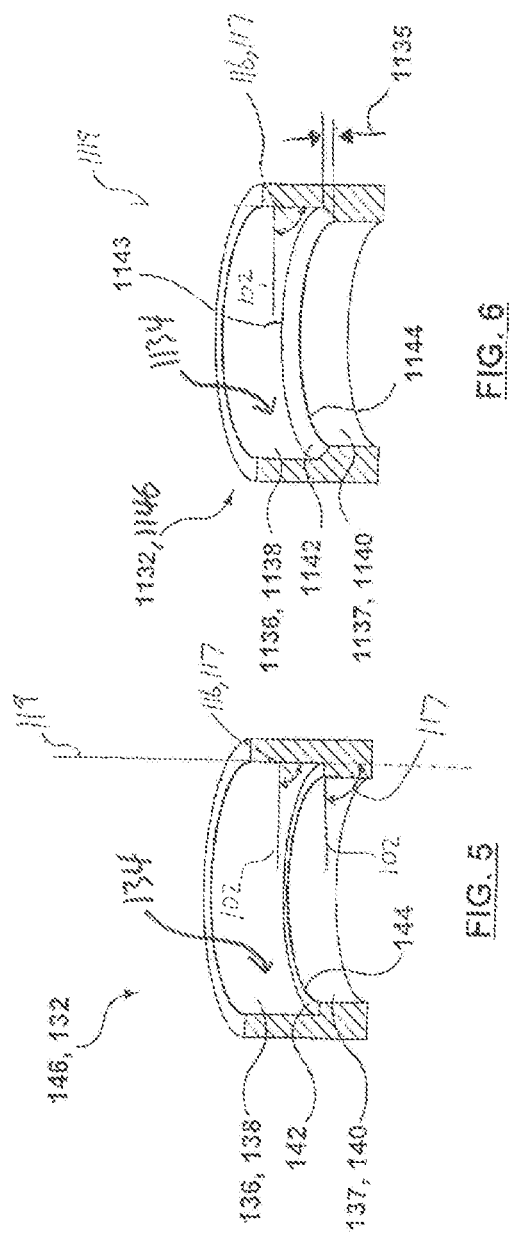

MENISCUS REDUCING MEMBER

CROSS-REFERENCE TO RELATED APPLICATION

This application is a continuation in part of U.S. patent application Ser. No. 14/760,397, which was filed Jul. 10, 2015 and which claims the benefit of 35 USC 120 based on the priority of U.S. Provisional Patent Application 61/751,012, filed Jan. 10, 2013, each of which are incorporated herein in their entirety by reference.

FIELD

Embodiments described herein relate to vessels for holding liquid and in particular to well-plates, and in particular to well-plates configured to reduce the magnitude of the meniscus curvature when aqueous liquids are placed within the wells.

BACKGROUND

US 2010/0067105 (Egeler et al.) discloses a meniscus reducing member for use in a vessel for containing a liquid including a surface feature overlying at least a portion of an interior surface of the vessel. The surface feature includes at least two surfaces for contacting the liquid that cooperate to reduce a width of a meniscus formed at an interface between the liquid and the surface feature by physically altering a contact angle between the liquid and the surface feature.

US 2010/0047845 (Woodside et al.) discloses methods of improving cell culture vessel assays. In one aspect the application is directed to a method of reducing the curvature of the meniscus comprising applying a coating material to the interior wall of the vessel, wherein the coating material provides a receding contact angle of about 90 degrees with aqueous solutions and culture media. In another aspect, the application is directed to a method of labeling cells in a first solution by generating droplets of a second solution containing at least one cell-labelling agent and allowing the droplets of the second solution to contact the surface of the first solution.

SUMMARY

This summary is intended to introduce the reader to the more detailed description that follows and not to limit or define any claimed or as yet unclaimed invention. One or more inventions may reside in any combination or sub-combination of the elements or process steps disclosed in any part of this document including its claims and figures.

Physical surface modifications to the interior wall surface of cell culture vessels that affect a reduced meniscus magnitude and a resultant diminished optical interference during imaging are described. The cell culture vessel can be any vessel including, without limitation, cell culture dishes or multiwell plates.

According to one broad aspect of the teachings described herein, a meniscus reducing member for use in a vessel for containing a liquid may include a physical surface feature overlying at least a portion of an interior surface of the vessel to engage a free surface of a liquid in the vessel. The physical surface feature may include first and second inner surfaces that are generally parallel to and spaced apart from each other and at least a third surface extending between the first and second surfaces. The third surface may be at an angle to and intersect both the first and second surfaces. The first, second and third surfaces may be configured to physically alter a receding contact angle between the liquid and the physical surface feature A coating material may be applied to at least one of the first inner surface, second inner surface and third surface of the physical surface feature. The coating material may be configured to chemically alter the receding contact angle between the liquid and the at least one of the first inner surface, second inner surface and third surface of the physical surface feature that is coated with the coating material, whereby the receding contact angle formed between the liquid and the first inner surface of the meniscus reducing member may be between about 75 degrees and 110 degrees.

The receding contact angle formed between the liquid and the first inner surface of the meniscus reducing member is between about 85 degrees and 95 degrees and optionally may be about 90 degrees.

The receding contact angle formed between the liquid and the first inner surface of the meniscus reducing member may be closer to 90 degrees than a receding contact angle formed between the liquid and the physical surface feature in the absence of the coating material.

The receding contact angle formed between the liquid and the first inner surface of the meniscus reducing member may be closer to 90 degrees than a receding contact angle formed between the liquid and a portion of the interior surface of the vessel coated with the coating material in the absence of the physical surface feature.

Alternatively, a coating material may be applied to at least one of the first inner surface, second inner surface and third surface of the physical surface feature. The coating material may be configured to chemically alter the receding contact angle between the liquid and the at least one of the first inner surface, second inner surface and third surface of the physical surface feature that is coated with the coating material, whereby the receding contact angle formed between the liquid and the first inner surface of the meniscus reducing member may be between about 90 degrees and less than 180 degrees.

The receding contact angle formed between the liquid and the first inner surface of the meniscus reducing member may be between about 110 degrees and 160 degrees.

The receding contact angle formed between the liquid and the first inner surface of the meniscus reducing member may be between about 120 degrees and 150 degrees.

The coating material may be hydrophobic or superhydrophobic.

The receding contact angle formed between the liquid and the first inner surface of the meniscus reducing member may be closer to 90 degrees than an intrinsic contact angle formed between the liquid and the meniscus reducing member.

The first inner surface may be positioned above the second inner surface when the liquid is contained in the vessel and a step edge may be defined by the intersection of the second inner surface and the third surface.

The first inner surface may be at least partially coated with the coating material and the second inner surface is substantially free from the coating material.

The second inner surface may be laterally inwardly offset from the first inner surface.

The third surface may be generally perpendicular to both the first and second inner surfaces.

The third surface may be inclined at an oblique angle to both the first and second inner surfaces.

The third surface may be substantially planar.

The coating material may be silicone based.

An intrinsic contact angle formed between the liquid and the first inner surface of the meniscus reducing member may be farther from 90 degrees than an unaltered intrinsic contact angle formed between the liquid and a portion of the interior surface of the vessel.

The receding contact angle between the liquid and the first inner surface of the meniscus reducing member may be closer to 90 degrees than an unaltered receding contact angle measured between the liquid an a portion of the interior surface of the vessel.

The coating material may include at least 63% by weight methyl perfluorobutylethyl siloxane, methylhydrogen siloxane, dimethyl siloxane and methyl vinly siloxane crosslinked with a crosslinking solution comprising at least 60% by weight trimethylsiloxy-terminated methyl(perfluorobutylethyl) siloxane, and trimethylsiloxy-terminated methylhydrogen siloxane.

The coating material may include at least one of a siloxane based coating and a nano-particle based coating.

The coating material may include at least one of Dehesive and FluoroPel.

According to another broad aspect of the teachings described herein, which may be used in combination with any other aspect of the teachings herein, a vessel may include a closed bottom wall and a sidewall extending from the bottom wall to an open top portion for retaining a volume of liquid within the vessel. The sidewall may include an interior surface. A physical surface feature may overlie at least a portion of an interior surface to engage a free surface of a liquid in the vessel. The physical surface feature may include first and second inner surfaces that are generally parallel to and spaced apart from each other and at least a third surface extending between the first and second surfaces. The third surface may intersect both the first and second inner surfaces. The first inner surface, second inner surface and third surface may be configured to physically alter a receding contact angle between the liquid and the meniscus reducing member. A coating material may be applied to at least one of the first inner surface, second inner surface and third surface of the physical surface feature. The coating material may be configured to chemically alter the receding contact angle between the liquid and the at least one of the first inner surface, second inner surface and third surface of the physical surface feature that is coated with the coating material, whereby the receding contact angle formed between the liquid and the first inner surface of the meniscus reducing member is between about 75 degrees and 110 degrees, or between about 90 degrees and less than 180 degrees.

The physical surface feature may be integral with the sidewall of the vessel.

The physical surface feature may be disposed on a separate insert member configured to be received within the vessel.

The physical surface feature may extend continuously around an inner perimeter of the vessel.

The surface feature may extend around only a portion of an inner perimeter of the vessel.

As applicable, the receding contact angle formed between the liquid and the first inner surface of the meniscus reducing member is between about 85 degrees and 95 degrees and optionally may be about 90 degrees.

Alternatively, the receding contact angle formed between the liquid and the first inner surface of the meniscus reducing member is, as applicable, between about 110 degrees and about 160 degrees, or between about 120 degrees and about 150 degrees.

The receding contact angle formed between the liquid and the first inner surface of the meniscus reducing member may be closer to 90 degrees than a receding contact angle formed between the liquid and the physical surface feature in the absence of the coating material.

The receding contact angle formed between the liquid and the first inner surface of the meniscus reducing member may be closer to 90 degrees than a receding contact angle formed between the liquid and a portion of the interior surface of the vessel coated with the coating material in the absence of the physical surface feature.

The coating material may be hydrophobic or superhydrophobic.

The receding contact angle formed between the liquid and the first inner surface of the meniscus reducing member may be closer to 90 degrees than an intrinsic contact angle formed between the liquid and the meniscus reducing member.

The first inner surface may be positioned above the second inner surface when the liquid is contained in the vessel and a step edge may be defined by the intersection of the second inner surface and the third surface.

The first inner surface may be at least partially coated with the coating material and the second inner surface is substantially free from the coating material.

The second inner surface may be laterally inwardly offset from the first inner surface.

The third surface may be generally perpendicular to both the first and second inner surfaces.

The third surface may be inclined at an oblique angle to both the first and second inner surfaces.

The third surface may be substantially planar.

The coating material may be silicone based.

An intrinsic contact angle formed between the liquid and the first inner surface of the meniscus reducing member may be farther from 90 degrees than an unaltered intrinsic contact angle formed between the liquid and a portion of the interior surface of the vessel.

The receding contact angle between the liquid and the first inner surface of the meniscus reducing member may be closer to 90 degrees than an unaltered receding contact angle measured between the liquid a portion of the interior surface of the vessel.

The coating material may include at least 63% by weight methyl perfluorobutylethyl siloxane, methylhydrogen siloxane, dimethyl siloxane and methyl vinly siloxane crosslinked with a crosslinking solution comprising at least 60% by weight trimethylsiloxy-terminated methyl(perfluorobutylethyl) siloxane, and trimethylsiloxy-terminated methylhydrogen siloxane.

The coating material may include at least one of a siloxane based coating and a nano-particle based coating.

The coating material may include at least one of Dehesive and FluoroPel.

According to another broad aspect of the teachings described herein, which may be used in combination with any other aspect of the teachings herein, a method of providing a meniscus reducing member for use in a vessel for containing a liquid may include the steps of:

a) providing a physical surface feature having first and second inner surfaces that are generally parallel to and spaced apart from each other and at least a third surface extending between the first and second surfaces, the third surface intersecting both the first and second inner surfaces, the physical surface feature configured to physically alter a receding contact angle between a liquid and the meniscus reducing member; and b) at least partially coating at least one of the first inner surface, second inner surface and the third surface with a surface coating material. The coating material may be configured to chemically alter the receding contact angle between the liquid and the meniscus reducing member.

The method may also include rotating the physical surface feature about a rotational axis while the coating material is being applied to the at least one of the first inner surface, second inner surface and the third surface.

The rotational axis may be at an angle of between about 0 degrees and about 5 degrees to a vertical axis.

The physical surface feature may be rotated about the rotational axis at a rate of between about 1 and about 25 revolutions per minute.

The method may also include mixing the coating material with a solvent prior to applying the coating material to at least one of the first inner surface, second inner surface and the third surface to reduce the viscosity of the coating material.

The method may also include the steps of evaporating at least a portion of the solvent and curing the coating material remaining on the at least one of the first inner surface, second inner surface and the third surface.

The coating material may be applied as a generally continuous bead of coating material on the at least one of the first inner surface, second inner surface and the third surface.

The method may also include the steps of axially translating the meniscus reducing member while the generally continuous bead of coating material is being applied to provide a generally helical bead of coating material on the at least one of the first inner surface, second inner surface and the third surface.

The coating material may be hydrophobic or superhyrdophobic.

The coating material may include at least one of a siloxane based coating, a nano-particle based coating, Dehesive and FluoroPel.

According to one broad aspect of the teachings described herein, a meniscus reducing member for use in a vessel for containing a liquid may include a physical surface feature overlying at least a portion of an interior surface of the vessel to engage a free surface of a liquid in the vessel. The physical surface feature may include first and second inner surfaces that are generally parallel to and spaced apart from each other and at least a third surface extending between the first and second surfaces. The third surface may be at an angle to and intersect both the first and second surfaces. The first, second and third surfaces may be configured to physically alter a receding contact angle between the liquid and the physical surface feature A coating material may be applied to at least one of the first inner surface, second inner surface and third surface of the physical surface feature. The coating material may be configured to chemically alter the receding contact angle between the liquid and the at least one of the first inner surface, second inner surface and third surface of the physical surface feature that is coated with the coating material, an interface angle formed between the liquid where it contacts the meniscus reducing member and a plane parallel to the first inner surface may be between about 75 degrees and 110 degrees, or may be between about 90 degrees and less than 180 degrees.

The interface angle formed between the liquid where it contacts the meniscus reducing member and a plane parallel to the first inner surface may be between about 85 degrees and 95 degrees and optionally may be about 90 degrees.

The interface angle formed between the liquid where it contacts the meniscus reducing member and a plane parallel to the first inner surface may be closer to 90 degrees than a receding contact angle formed between the liquid and the physical surface feature in the absence of the coating material.

The interface angle formed between the liquid where it contacts the meniscus reducing member and a plane parallel to the first inner surface may be closer to 90 degrees than a receding contact angle formed between the liquid and a portion of the interior surface of the vessel coated with the coating material in the absence of the physical surface feature.

The coating material may be hydrophobic or superhydrophobic.

The interface angle formed between the liquid where it contacts the meniscus reducing member and a plane parallel to the first inner surface may be closer to 90 degrees than an intrinsic contact angle formed between the liquid and the meniscus reducing member.

The first inner surface may be positioned above the second inner surface when the liquid is contained in the vessel and a step edge may be defined by the intersection of the second inner surface and the third surface.

The first inner surface may be at least partially coated with the coating material and the second inner surface is substantially free from the coating material.

The second inner surface may be laterally inwardly offset from the first inner surface.

The third surface may be generally perpendicular to both the first and second inner surfaces.

The third surface may be inclined at an oblique angle to both the first and second inner surfaces.

The third surface may be substantially planar.

The coating material may be silicone based.

An intrinsic contact angle formed between the liquid and the first inner surface of the meniscus reducing member may be farther from 90 degrees than an unaltered intrinsic contact angle formed between the liquid and a portion of the interior surface of the vessel.

The receding contact angle between the liquid and the first inner surface of the meniscus reducing member may be closer to 90 degrees than an unaltered receding contact angle measured between the liquid an a portion of the interior surface of the vessel.

The coating material may include at least 63% by weight methyl perfluorobutylethyl siloxane, methylhydrogen siloxane, dimethyl siloxane and methyl vinly siloxane crosslinked with a crosslinking solution comprising at least 60% by weight trimethylsiloxy-terminated methyl(perfluorobutylethyl) siloxane, and trimethylsiloxy-terminated methylhydrogen siloxane.

The coating material may include at least one of a siloxane based coating and a nano-particle based coating.

The coating material may include at least one of Dehesive and FluoroPel.

DRAWINGS

FIG. 1*a* is a cross-section view of a vessel containing a fluid having a contact angle less than 90 degrees;

FIG. 1*b* is a cross-section view of a vessel containing a fluid having a contact angle equal to 90 degrees;

FIG. 1*c* is a cross-section view of a vessel containing a fluid having a contact angle greater than 90 degrees;

FIG. 2 is an illustration of a liquid droplet on a surface defining a contact angle;

FIG. 5 is a cross-section view of an insert for a vessel including a meniscus reducing member having a flat step-like surface feature;

FIG. 6 is a cross-section view of an insert for a vessel including a meniscus reducing member having a sloped step-like surface feature;

DETAILED DESCRIPTION

Figure 1A:
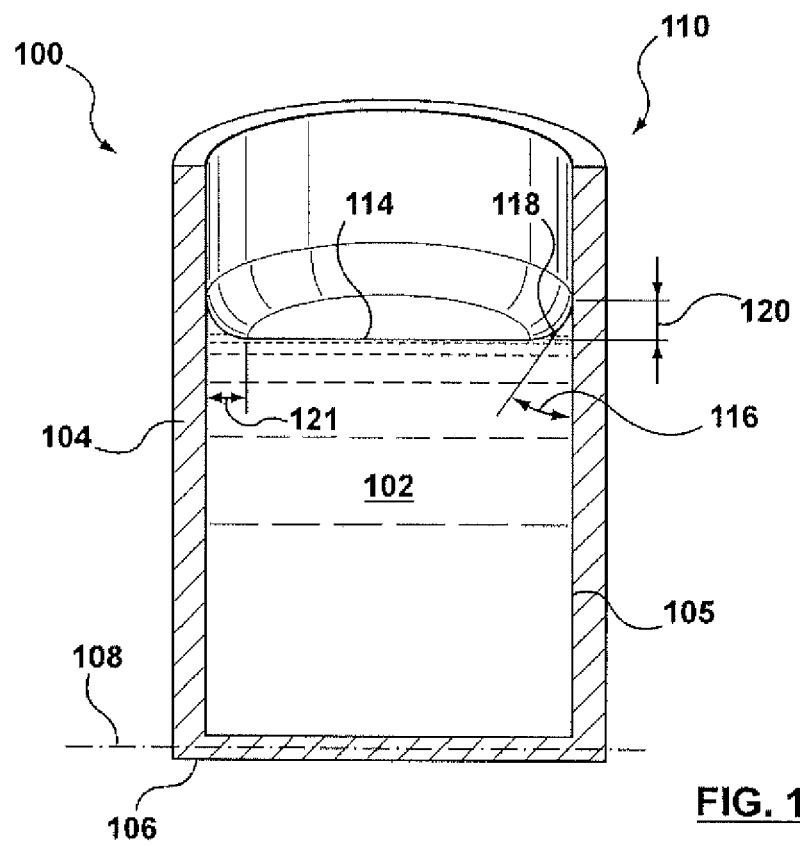

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

When a liquid is placed on a solid surface, the liquid surface assumes a shape that is characteristic of the physiochemical properties of the three phases involved (solid, liquid and vapor phase). The angle defined by the liquid and solid surfaces at the point of contact of the three phases is termed the "contact angle" (θ). The magnitude of this angle is determined by the interfacial free energies (surface tension, γ) of the liquid-vapor (LV) interface, the liquid-solid (LS) interface, and the solid-vapor (SV) interface. In the case of liquids placed within a dish or well of a multiwell plate, a meniscus results when the contact angle between the liquid and the solid surface is other than 90 degrees. When the contact angle is less than 90 degrees, a concave meniscus is formed, and when the contact angle is greater than 90 degrees, a convex meniscus is formed.

Due to the contact angle properties defined above, surface energies of the solution and the containing solid interfaces are often cited as defining properties that determine meniscus shape and magnitude (for example meniscus width, height and/or % area). However, physiochemical properties, in addition to surface energies of the liquid and solid surfaces, are of importance in determining meniscus shape of aqueous liquids at equilibrium. Such properties include (a) the three-dimensional topology of the solid surface, (b) the composition of the liquid phase, (c) physical and chemical heterogeneity of the solid surface, and (d) inducibility of configurational changes of the solid surface by the liquid. This causes a hysteresis in contact angles dependent on the interactions of the above mentioned surface properties, which makes the theoretical estimation of meniscus magnitude difficult based on surface chemistries. The inventors are not currently aware of any universal theory which accurately models the contact angle in complex systems, and thus contact angle hysteresis and the resulting meniscus are typically determined empirically for different liquid/solid combinations.

A meniscus can present a problem to optical imaging of the objects present within a liquid containing vessel, dish or well for several reasons. The curvature of the liquid surface will cause the refraction and reflection of the illuminating light and result in optical interference within the area of the meniscus. In addition, the meniscus results in a change in liquid depth near the solid surfaces and may cause an uneven distribution of objects near the wall of the dish or well.

Several methods have been used to compensate for meniscus effects in digital microscopy. Observations can be limited to central portions of a well or the light exposure can be increased when imaging within the meniscus. Physical barriers, such as coverslips, have also been used to compress the meniscus. However, such methods are cumbersome and can reduce the sampled image area so as to omit relevant areas of cell cultures and render the method not quantitative.

One technique for mitigating meniscus formation is to apply a coating to an otherwise smooth vessel wall that provides desirable surface properties at the liquid-solid interface between a particular coated wall surface and a particular liquid so as to result in a dynamic minimum contact angle of approximately 90 degrees. However, since these surface properties of the liquid-solid interface are dependent on the complex interactions between physicochemical properties of the liquid as well as the solid surface chemical and physical heterogeneity, different wall polymers or surface coatings would be required for liquids with dissimilar properties. In addition, it can be difficult to apply the coating to the wall of the vessel only, without getting the coating on the vessel bottom. Coating the bottom of the vessel can result in incomplete wetting of the vessel bottom, which then will cause a strong concave meniscus and interfere with microscopy.

Another technique for mitigating meniscus formation is to create physical features on the vessel wall that results in the meniscus being held at a specific level, or by creating regions of alternating convex and concave meniscus that result in an effective flat meniscus when evaluating optical interference. A disadvantage of the former solution may be that meniscus reduction only works for a specific fluid volume and can exhibit meniscus formation if the wall above the feature is wetted by the fluid such as occurs during routine handling of culture vessels. A disadvantage of the latter solution is that manufacturing can be complex.

A method that is effective for reducing meniscus magnitude with a wide variety of aqueous solutions having various surface energies, and where the reduced meniscus is maintained during routine handling, would be advantageous for many imaging and biological applications.

For an ideal, homogenous surface, the magnitude of the theoretical or intrinsic contact angle is given by Young's equation:

$$\gamma_{LV} \cos \theta = \gamma_{SV} - \gamma_{SL} \qquad (1)$$

For the purposes of the present application, the liquid phase is considered to be an aqueous solution, in particular viscous aqueous solutions comprising biopolymers such as proteins, peptides and polysaccharides, or cell culture media.

As explained in detail above, properties that can affect the contact angle formed between a liquid and a solid surface can include (a) the three-dimensional topology of the solid surface, (b) the composition of the liquid phase, (c) physical and chemical heterogeneity of the solid surface, and (d) inducibility of configurational changes of the solid surface by the liquid. Properties (c) and (d) above effect an influence on meniscus shape by causing contact angle hysteresis, defined as the discrepancy between the maximum and minimum contact angles observed for a liquid drop when the point of contact of the liquid, solid, and vapour phases is advanced and retreated across the solid surface. When the liquid advances over the solid surface, the contact angle is observed to be greater than when the liquid retreats from the solid surface. These "advancing" and "receding" contact angles are taken as the dynamic maximum and dynamic minimum contact angles, respectively, and their difference is referred to as the contact angle hysteresis. This hysteresis is caused by the energies required to overcome the heterogeneity in hydrophobic and hydrophilic domains on the surface (chemical heterogeneity), or overcome physical barriers on the solid surface (physical heterogeneity, or surface "roughness").

In the case of chemical heterogeneity, as an aqueous solution advances over a surface, hydrophobic domains on the surface will impede the motion of the solution and result in an increase in contact angle, whereas as when the solution recedes from the surface, hydrophilic domains on the surface will retain the liquid on the surface, resulting in an increased contact angle.

In the case of physical heterogeneity, microscopic variations in the surface will impede the motion of the solution providing resistance to the advancing front of the liquid (thus increasing contact angle), and hold back the receding boundary of the liquid-solid surface as the liquid recedes (thus decreasing contact angle).

Configuration changes of the solid surface brought on by contact with the liquid phase introduces additional hysteresis into observed contact angles. The change in surface configuration is a result of the reorientation of functional groups on a polymeric solid surface when exposed to the liquid in order to minimize interfacial tension at the surface between the solid and liquid phases. This reorientation is thought to consist primarily of a rotation of the surface functional groups about the molecular axis, rather than a rearrangement of the macromolecular structure of the polymer. The result is that portions of the solid surface that have been exposed to the liquid phase (ie. have been "wetted") will exhibit an altered surface energy. In the case of aqueous liquids in contact with the surface of a solid hydrophobic polymer, the wetted surface is expected to exhibit a reduced hydrophobicity compared to non-wetted surfaces, due to rotation of hydrophobic moieties away from the surface. Thus, when the liquid phase recedes over a wetted surface, a reduced contact angle results compared to the static contact angle of the liquid on a non-wetted surfaces. This further contributes to the altered magnitude of a receding contact angle.

Composition of the aqueous solution is likely to affect contact angle hysteresis. For example, presence of components that modulate the hydrophobic and hydrophilic interactions between the liquid and solid surfaces, or alter the surface energies of the liquid-vapour and liquid-solid interfaces are likely to affect the hysteresis. The presence of molecules with polar and non-polar regions, such as surfactants, phospholipids, or fatty acids, may be expected to modulate interactions between hydrophobic and hydrophilic moieties on the solid surface and the aqueous liquid. Such molecules may also exert varying effects on the configuration of the surface functional groups of the solid phase, further altering contact angle. Furthermore, solubilized components may adhere to the solid surface, altering its surface energy and affecting the contact angle. For example, albumin-containing solutions have been shown to affect contact angles of the solution with hydrophobic surfaces due to protein adsorption to the surface. In addition, composition of the aqueous solution may affect the viscosity of the liquid and hence the energy required to return the system to its equilibrium state after a physical disturbance (i.e. highly viscous solutions result in altered contact angles at equilibrium, compared to similar solutions of lower viscosity).

Advancing and receding contact angles are commonly determined by one of two methods: (1) The sessile drop method whereby a drop of the liquid phase is placed on the solid surface. In this case, the advancing angle is obtained by addition of volume to the drop and a receding angle is obtained by removal of volume from the drop. (2) The Wilhelmy plate method, whereby a polymeric surface is slowly immersed in the liquid phase (resulting in the advancing contact angle) and then withdrawn from the surface (resulting in the receding contact angle). These methods result in different absolute contact angles, due the sessile drop method having a stationary horizontal surface, and the Wilhelmy plate method having a moving vertical surface.

For the purpose of clarity, meniscus formation of a liquid will be discussed in a cylindrical tube, although the above mentioned aspects of contact angle and meniscus apply to containers of a variety of shapes (eg. square, round, or triangular tubing, wells, or other containers). Typically, when an aqueous solution is placed in a hydrophobic cylinder, the shape of the meniscus is dictated by the advancing contact angle as the level of the liquid rises within the cylinder. For an ideal homogenous surface, when addition of the liquid is complete, the shape of the meniscus will come to equilibrium as dictated by the intrinsic contact angle of the system as defined by Young's equation (above). However, in real-world applications, ideal homogenous surfaces are unlikely. As such, contact angle hysteresis will come into play if the system is not completely static. Further, any physical disturbance of the container, such as vibration, rotation, or acceleration/deceleration due to movement of the container can result in movement of the liquid level and the three-phase contact line (i.e. the intersection of the solid, liquid, and vapour phases) will be subjected to a cycle of advancing and receding contact angles. Following such a cycle, a new equilibrium contact angle is established. The new equilibrium contact angle may not be represented by Young's intrinsic contact angle, but instead may be represented by the receding contact angle of the solution on the wetted surface. Currently, the inventors are not aware of any universal theory which accurately models this contact angle in complex systems, and thus the receding contact angle and the resulting meniscus is best determined empirically for different systems (see examples hereinbelow).

Generally, in a completely static system for typical aqueous solutions contained by solid surfaces, the meniscus shape is defined by the intrinsic contact angle as predicted by Young's equation. However, such static systems are very rarely encountered in routine laboratory tasks, especially since procedures involving solutions commonly require physical mixing after addition to a container. In the more common scenario, where the liquid surface is subject to physical disturbance, the meniscus shape is sensitive to contact angle hysteresis, topology of the interior wall surface of the container, and composition of the aqueous solution. It is believed that the receding contact angle of the system is the primary indicator of meniscus shape and magnitude under real working conditions. Consequently, while an intrinsic contact angle of 90 degrees will be characteristic of perfectly flat meniscus in a completely static system, a receding contact angle of 90 degrees is required to maintain a flat meniscus in a system subject to physical disturbance, as commonly encountered in most real-world applications.

One limitation of current assay vessels and well-plates is that the meniscus on the medium at the circumference of the dish or well causes optical distortion around the circumference of the plate. In this area it is more challenging to see the cells or colonies using a visible light microscope in visible light transmission or darkfield mode or in fluorescent mode. Images acquired using a camera and static optics, or using moving optics such as in a scanner, show the meniscus effect. The pattern recognition ability of the human brain can handle the varying background and human observers are able to identify the entities in the images or under a microscope. However, it is easier to identify the entities where there is no meniscus. In addition, computer-based image analysis is much more challenging when the background is variable because common approaches use the difference in intensity or brightness between the background and foreground to distinguish objects. Thus there is an advantage to eliminating optical interference due to the meniscus for both manual and automated imaging of cells and other entities in culture wells or culture vessels. This advantage would extend to any assay where optical or spectroscopic measurements or observances are made, including for example, fluorescence-, UV light-, infrared light- and visible light-based assays.

It has been shown that if the vertical walls of a culture vessel exhibit surface energies that result in an intrinsic contact angle of approximately 90 degrees, the magnitude of the meniscus of the culture media is minimized, which in turn reduces the dark rim generally seen around the edge of the culture vessel. Furthermore, it has been shown that physical disturbance to common aqueous solutions and culture media within the culture vessel results in formation of a meniscus. This is due to contact angle hysteresis commonly exhibited with interfaces of aqueous solutions and solid surfaces.

It has also been shown that if the walls of culture vessels are treated so as to provide a receding contact angle of about 90 degrees, the meniscus reducing features of the surfaces are robust to physical disturbance and prolonged incubation. This improves the ability of manual operators and automated systems to distinguish entities near the rim of the culture vessel.

Figure 1B:
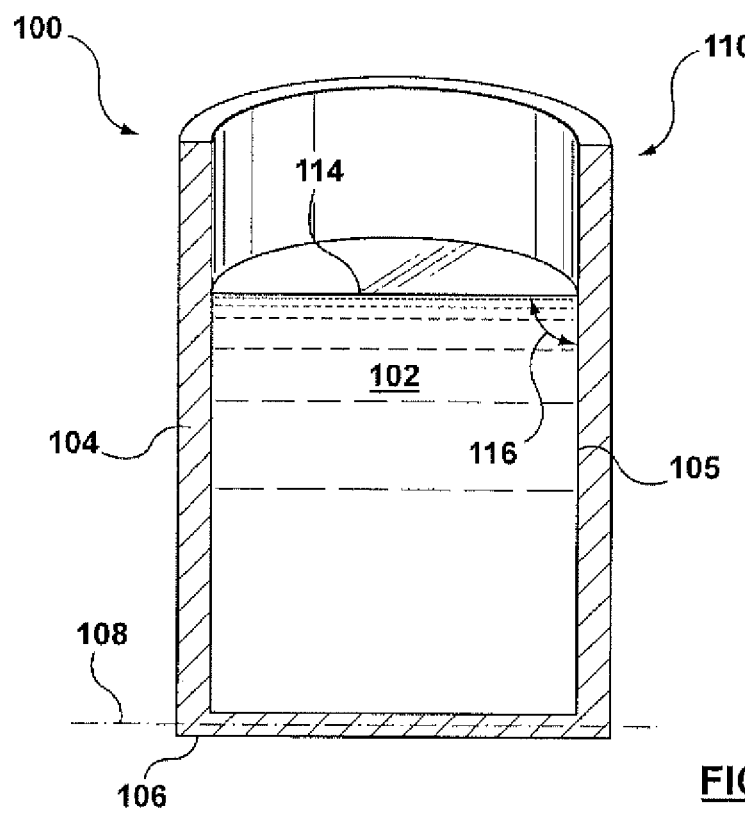
Figure 1C:
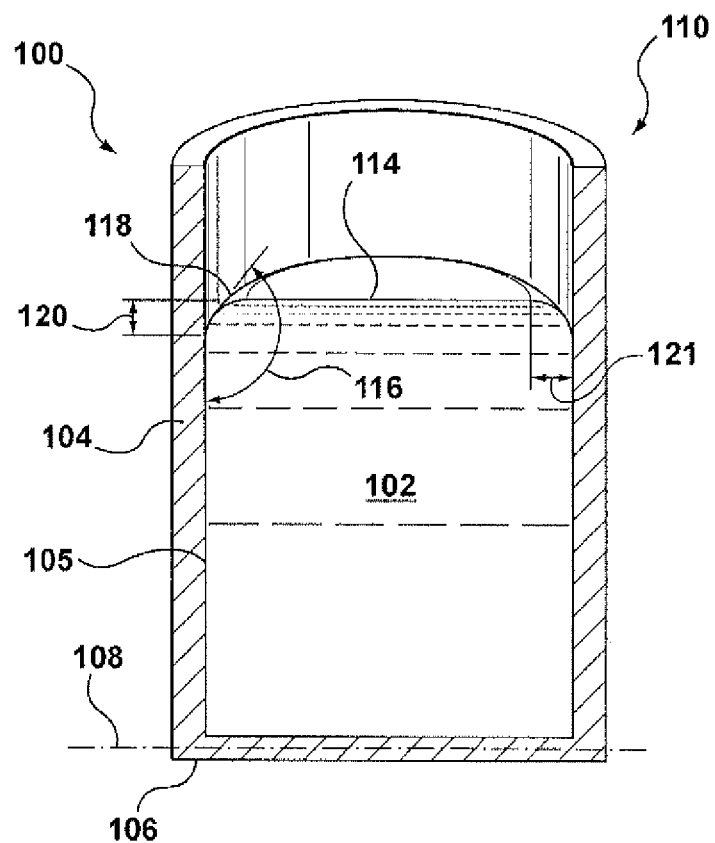

Referring to FIGS. 1a-1c, an example of a vessel 100 containing a liquid 102 is illustrated. For clarity and ease of description, in this application the vessel 100 is described as a cylindrical vessel or tube having a sidewall 104 and a bottom 106 discusses meniscus formation of the liquid in a cylindrical tube that comprises the solid phase. However, it is understood that the vessel 100 may be any suitable shape (e.g. square, round, or triangular tubing, wells, or other containers) and may have a greater or fewer number of sidewalls 104 (for example a square container could have four orthogonal sidewalls). While the vessel sidewalls 104 are illustrated as being vertical, it is understood that in some examples at least a portion of each sidewall 104 may be inclined, curved or otherwise shaped. The sidewalls 104 further comprise an inner or interior surface 105 for contacting the liquid 102 retained in the vessel 100.

In the present example the vessel bottom 106 is flat, as illustrated, while in other examples the vessel bottom 106 may be sloped, concave, convex or any other suitable shape. Regardless of the actual shape of the vessel bottom 106, the vessel 100 defines a lower plane 108 that is spaced apart from the upper end of the vessel 110 and intersects the vessel sidewalls 104 at the same orientation as a flat vessel bottom 106. In the present example the vessel bottom 106 lies within the lower plane 108. In other examples having non-flat bottoms, the vessel bottom 106 may not coincide with the lower plane 108.

The vessel 100 may be constructed from any material suitable material. Optionally, the material can be selected such that it is suitable for the introduction of micro-surface topologies or the application of hydrophilic, hydrophobic and superhydrophobic surface coatings. Examples of suitable materials include polymeric materials, polystyrene, polypropylene, polycarbonate, polyvinylchloride, polytetrafluoroethylene, or other suitable polyolefin or similar solid polymeric substrate.

The hydrophobic coating materials could for example be silicone based, fluoropolymer based, petroleum jelly, or paraffin wax. Superhydrophobic coatings could consist of nanostructured films, for example films of nanotubes composed of silica, carbon, or perfluorocarbon polymers. Such coatings are known in the art as nanotube "carpets", "forests", or "films". Nanostructured films could also consist of other regularly or irregularly organized molecular assemblies resulting in nanofeatured surfaces.

As exemplified, the vessel 100 is configured to retain a volume of liquid 102. The liquid 102 has a free surface or upper surface 114 that has a liquid surface tension. The properties and characteristics of the liquid surface tension may depend on the composition of the liquid. Examples of liquids 102 that may be contained within the vessel 100 include aqueous solutions of salts, sugars, proteins, glycoproteins, polysaccharides, methylcellulose, agar, collagen, or other similar gelling agents.

Referring to FIG. 1a, at the interface between the interior surface 105 of vessel sidewall 104 and the free surface of the liquid 114, the peripheral portions of the liquid surface may engage the interior surface 105 of the vessel 100 at a different level within the vessel 100 than the free surface level 114. The difference in surface level between the free surface 114 and the liquid-sidewall interface is referred to as meniscus 118 having a meniscus magnitude 120. The distance from the interior surface 105 to the point where the liquid surface 114 is essentially planar defines a meniscus width 121. The angle between the vessel side wall 104 and the liquid surface in the meniscus 118 region defines a contact angle 116. If the contact angle 116 is less than 90 degrees, as shown in FIG. 1a, the meniscus is considered a concave meniscus 118. If the contact angle is greater than 90 degrees, as shown in FIG. 1c, the meniscus is considered a convex meniscus 118. If the contact angle is equal to 90 degrees, as shown in FIG. 1b, the meniscus magnitude 120 (shown in FIGS. 1a and 1c) is zero, the meniscus width 121 is zero, and the liquid is described as having no meniscus 118.

For a given liquid/solid interface (i.e. the interface between liquid 102 and sidewall 104), the magnitude of the meniscus 120 formed may be altered by modifying the contact angle 116 created between the liquid 102 and the sidewall 104. The present application relates to a meniscus reducing member that physically alters the contact angle 116 formed between liquid 102 and the meniscus reducing member so that the contact angle 116 between the liquid 102 and the meniscus reducing member is closer to 90 degrees than the contact angle 116 between the liquid 102 and the original sidewall 104 material. Reducing the meniscus magnitude 120 by altering the contact angle 116 between the liquid 102 and the sidewall 104 may be understood as compensating for the contact angle effects or compensating for the contact angle between the liquid 102 and a surface.

One example of a method for measuring the contact angle 116 between a liquid 102 and a solid surface 122 is described with reference to FIG. 2. FIG. 2 illustrates a drop of liquid 102 resting on a substantially horizontal surface 122. In order to quantify contact angles 116 at the three-phase (solid substrate-aqueous liquid-air) interfaces, a 20 µL droplet of the liquid 102 was slowly placed onto the surface 122. Lateral view images of the droplet 102 resting on the surface were captured with the use of a Lumenera digital camera and a 0.6× magnification lens. The lens was oriented horizontally facing the drop 102, at a level even with the solid surface 122. Illumination was provided by backlighting with an amber LED behind an opaque diffuser. Image capture conditions were maintained at constant settings (Gain 1, exp. 0.3 s, acquisition resolution 2080×1536). The dynamic minimum contact angles 116 were determined by image capture after increasing the droplet volume to 40 µL and then removing 20 µL to recede the contact line over the surface. Images were captured within 2 to 5 seconds of droplet 102 manipulation.

The contact angle 116 was determined by analysis of lateral view images. Briefly, the horizontal plane (droplet baseline) of the image was established by drawing a straight line 124 through the contact points of the droplets with the surface 122. A best fit circle 126 is drawn through perimeter points of the droplet 102 near the contact points 128 of the left and right margins of the droplet 102 with the surface. This circle 126 is intended to be a best fit to the curvature of the surface of the droplet 102 near the contact point 128. The angle between 124 and the tangent line 130 to the best fit circle 126 at contact point 128 is taken to be the contact angle 116.

For a given liquid/solid interface (i.e. the interface between liquid 102 and sidewall 104), the magnitude of the meniscus 120 formed may be altered by modifying the contact angle 116 created between the liquid 102 and the sidewall 104. The present application relates to a meniscus reducing member that physically alters the contact angle 116 formed between liquid 102 and the meniscus reducing member so that the contact angle 116 between the liquid 102 and the meniscus reducing member is closer to 90 degrees than the contact angle 116 between the liquid 102 and the original sidewall 104 material. Reducing the meniscus magnitude 120 by altering the contact angle 116 between the liquid 102 and the sidewall 104 may be understood as compensating for the contact angle effects or compensating for the contact angle between the liquid 102 and a surface.

One aspect of the teachings herein relates to a meniscus reducing member that includes modifying the chemical composition of the polymeric wall surface or providing a coating material on the interior wall surfaces of the culture vessel, to chemically modify the contact angle between the liquid and the interior wall surfaces to help provide a receding contact angle of between about 75 and about 105 degrees, and preferably between about 80 and about 100 degrees, and more preferably of about 90 degrees with aqueous solutions and culture media.

Another aspect of the teachings herein relates to a meniscus reducing member that includes modifying the chemical composition of the polymeric wall surface or providing a coating material on the interior wall surfaces of the culture vessel, to chemically modify the contact angle between the liquid and the interior wall surfaces to help provide a receding contact angle of between about 90 and less than 180 degrees, and preferably between about 110 and about 160 degrees, and more preferably between about 120 degrees and about 150 degrees with aqueous solutions and culture media.

In addition to modifying the chemical composition of the polymeric wall surface or coatings of the surface for the reduction of meniscus formation, another aspect of the teachings described herein relate to physical surface feature type meniscus reducing members that reduce the magnitude of a meniscus formed within a vessel by physically interfering with meniscus formation. Examples of such a meniscus reducing member include a surface feature that is introduced onto the interior wall surface of a liquid containing vessel or well to physically interfere with meniscus formation. Examples of such surface features are explained in greater detail herein.

The inventors have advantageously discovered that both aspects described herein may be used in combination with each other. Preferably, a vessel can be provided with a meniscus reducing member that includes a combination of both physical and chemical/surface coating type meniscus-controlling features to help provide a desired receding contact angle. This may help provide a desired receding contact angle between the vessel and a variety of different solutions, each having different chemical and/or physical properties. This may allow the same vessel to be used in combination with a variety of different solutions while still providing a reducing meniscus angle that is within the desired range, and preferably is close to 90 degrees. This may help reduce the number of different vessels required by a user to accommodate different liquids and may help reduce testing costs.

In this configuration, at least one contact angle (for example either the intrinsic angle or the receding angle or both) formed between a chemically coated, physical surface feature is closer to the desired value (e.g. 90 degrees) than the corresponding contact angle formed between the same liquid and either i) a physical surface feature that is not coated with the coating material, and ii) a portion of a vessel wall that is coated with the chemical coating material but is otherwise smooth and does not include a physical surface features as described herein.

Optionally, a meniscus reducing member having the combination of both physical surface features and a chemical coating material may be configured to help provide an interface angle between the surface of the liquid where it contacts the meniscus reducing member and a generally vertical plane that is between about 75 degrees to about 110 degrees, about 80 degrees to about 110 degrees, about 85 degrees to about 105 degrees, and preferably of about 90 degrees (i.e. a generally flat meniscus) with aqueous solutions and culture media. Alternatively, a meniscus reducing member having the combination of both physical surface features and a chemical coating material may be configured to help provide an interface angle between the surface of the liquid where it contacts the meniscus reducing member and a generally vertical plane that is between about 90 degrees and less than 180 degrees, about 110 degrees to about 160 degrees, or about 120 degrees to about 150 degrees. In some examples, the interface angle may be the receding contact angle between the aqueous solutions or culture media and the meniscus reducing member. In other examples, the interface angle may be the sum of a receding contact angle between the aqueous solutions or culture media and an inclined portion of meniscus reducing member, and the angle of inclination of such an inclined portion (i.e. the sum of the angle of a surface being contacted, and the contact angle between the fluid and the surface). Optionally, the coating material may be selected to inhibit adhesion of molecular constituents present in aqueous solution or cell culture medium. This may help prevent alteration of the surface properties of the coating. When referring to the interface between a liquid and a generally vertical surface, the terms interface angle and contact angle may be used interchangeably for the purposes of this description.

Figure 3:
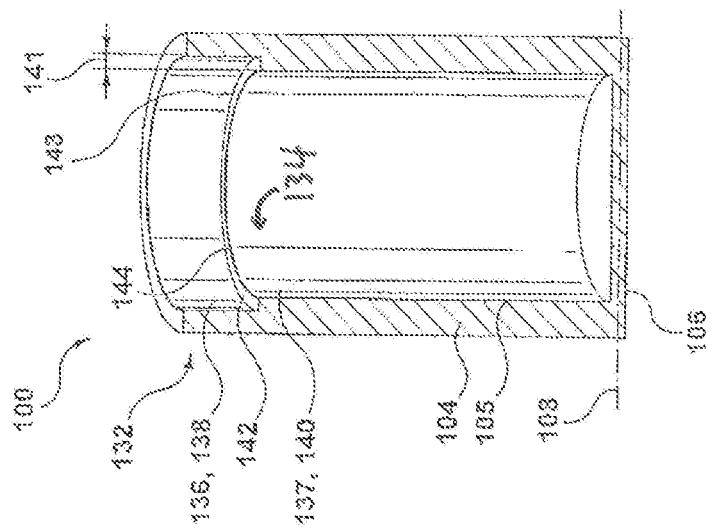
FIG. 3 is a cross-section view of a vessel including a meniscus reducing member having a flat step-like surface feature.

Referring to FIG. 3, a vessel 100 can be provided with a meniscus reducing member 132. In the illustrated example, the meniscus reducing member 132 includes a physical surface feature 134 overlying at least a portion of an interior surface 105 of the vessel 100.

The physical surface feature 134 preferably includes at least two different surfaces 136, 137 that are laterally spaced apart from each other and may be configured for contacting the liquid 102 in the vessel 100. The at least two surfaces 136, 137 cooperate to reduce a magnitude of a meniscus 120 and meniscus width 121 (shown in FIGS. 1a and 1c) formed at an interface between the liquid 102 and the physical surface feature 134 by physically altering or compensating for the contact angle 116 between the liquid 102 and the physical surface feature 134.

Referring to FIG. 3, in the illustrated example the physical surface feature 134 is a step-like feature in which the at least two surfaces 136, 137 include the first and second surface 138, 140 and a generally upward facing step face 142 extending therebetween (in this application "upward", "upper" and other similar terms are generally used to refer the direction toward the open, upper end of the vessel 110). Optionally, as explained in greater detail below, faces 138 and 140 may be portions of the vessel inner face 105 that are positioned around the expect fill level of the liquid in the vessel 100, or may be provided on a separate member, such as an insert. In the illustrated example, the step face 142 extends between and connects the first and second faces 138, 140. A step corner 143 is defined between the laterally outer edge of the step face 142 and the first face 138 and a step edge 144 is defined by the intersection of the second face 140 and the step face 142.

In the example illustrated in FIG. 5, if the liquid 102 is at a level such that it is above the step face 142 and directly engages the first inner surface 138, the interface angle 117 is the receding contact angle 116 between the liquid and a plane 119 containing the first inner surface 138 (a generally vertical plane in the example illustrated). Alternatively, if the liquid 102 is at a level such that the surface of the liquid 102 engages step edge 144 (i.e. does not actually contact the first inner surface 138) the interface angle 117 can still be measured with respect to the plane 119 despite the fact that the liquid 102 does not actually "contact" the first inner surface 138.

Optionally, as shown in FIGS. 3 and 5, the step face 142 can be a generally flat, upward facing surface that is generally horizontal and generally perpendicular to the first and second inner faces 138, 140.

In this configuration, it has been observed that if the liquid level is below the step face 142 a generally concave meniscus is produced and that if the liquid level is at or above the step face 142 (i.e. the surface of the liquid engages the step face 142) then the meniscus is generally flatter. In the illustrated examples (including other embodiments described herein) it may be advantageous to position the meniscus reducing members (and/or to control the amount of liquid within the vessel) so that the surface of the liquid engages the step face 142 (or face 1142 as described herein, etc.) or is set/pinned at the level of the step edge 144.

Figure 4:
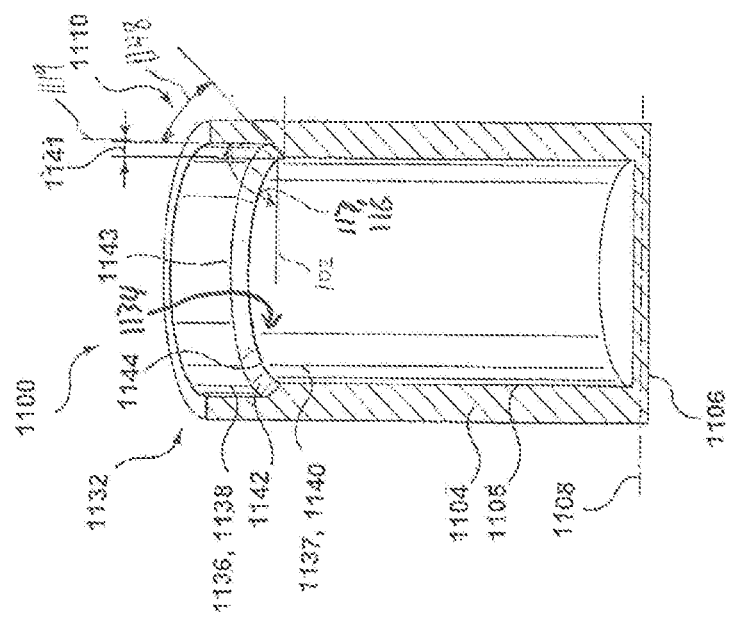
FIG. 4 is a cross-section view of a vessel including a meniscus reducing member having a sloped step-like surface feature.

Alternatively, FIG. 4 illustrates another example of a vessel 1100 that includes a meniscus reducing member 1132. Vessel 1100 may be generally similar to vessel 100, and analogous features are identified using analogous reference numerals indexed by 1000. In FIG. 4, the step face 1142 is an angled or sloped surface that is at an oblique angle to the first and second faces 1138, 1140, of the inner surface having a slope angle 1148.

Meniscus formation within the vessel may be inhibited (i.e. the contact angle 116 may approach 90 degrees and the meniscus magnitude 120 may approach zero) by including a physical surface feature 1134 overlying at least a portion of an interior surface 1105 of vessel 1100 which may comprise a step face 1142 (i.e. a step-like physical surface feature 1134) at a given position around the inner perimeter of the interior surface 1105 surface of the vessel 1100. In the illustrated examples, the step faces 142 (1142) of the physical surface features 134 and 1134 are located toward the upper ends 110 and 1110 of the vessels 100 and 1100. Alternatively, step faces 142 (1142) of the the physical surface features 134 and 1134 may be located in other positions within the vessels 100 and 1100. Optionally, the physical surface features may extend continuously around the entire inner perimeter of the vessel in which they are located (as illustrated). Alternatively, the physical surface features may be configured to extend only part way around the inside of the vessel.

When a liquid contacts the step-like physical surface feature 134, as shown in FIGS. 3 and 5, the meniscus formed at the interface between the interior surface 105 and the liquid is diminished as the level of liquid in the container approaches the step edge 144 of the physical surface feature 134. To form a meniscus between the liquid 102 and the vessel 100, the liquid 102 must be in physical contact with the interior surface 105 of the vessel 100 and the meniscus magnitude 120 (shown in FIGS. 1a and 1c) cannot exceed the distance between the free surface of the liquid 114 and the upper end of the vessel 110. The step-like physical surface feature 134 acts as a virtual or imitation upper edge of the vessel. As the surface level of the liquid 102 increases within the vessel 100, the distance between the liquid surface 114, the step edge 144 and step face 142 decreases, thereby reducing the available portion of the second inner portion 140 that can support the meniscus. When the level of the liquid contained in the vessel is equal to the position of the step edge 144, a flat liquid-vapor interface (i.e. an interface angle 117 of 90 degrees) will result, regardless of the intrinsic contact angle 116 of solid-liquid-vapor interface (i.e. the contact angle 116 between the liquid 102 and a flat surface 122 made from the physical surface feature 134 material). If the step face 142 is horizontal, to achieve the desired 90 degree interface angle 117 the level of the liquid can be substantially aligned with the step edge 144. Setting the liquid level to be generally aligned with the step edge 144 may help provide a desired interface angle 117.

The meniscus reducing capability of the step-like physical surface feature 134 may be most effective when the free surface of the liquid is generally level with the step edge 144 or some part of the sloped step face 142. If the free surface of the liquid is level with the step edge 144 then the tangent line 130 (as shown in FIG. 2) will be parallel to the step edge 144 (i.e. generally 90 degrees to the surface 136 and plane 119).

In the present example, the first and second inner faces 138, 140 are generally orthogonal to the lower plane 108 (i.e. generally vertical when the vessel is in an upright position) and the second inner face 140 is laterally inwardly offset from the first inner face 138 by an offset distance 141 (shown in FIG. 3). The offset distance 141 may be greater than 0.1 mm and in the present example is about 0.75 mm. Both the first and second inner faces 138, 140 have a generally annular shape and are concentrically aligned. When reference is made to a plane that contains the first or second inner surfaces 138, 140 it is understood that it is a plane that is tangential to the respective surface 138, 140 at the location of measurement.

Referring to FIG. 4, when a liquid contacts the physical surface feature 1134 of vessel 1100, as shown in FIGS. 4 and 6, the meniscus magnitude 120 (FIG. 1*a*) may be reduced due to compensation of the intrinsic contact angle 116 of the 3-phase contact line by the slope of the step face 1142, represented by angle 1148. This may help modify the interface angle toward 90 degrees, but may be less effective than the combination of the sharp corner 144 and horizontal face 142 as shown in FIGS. 3 and 5. However, modifying angle 1148 of angled face 1142 may increase the height 1135 (FIG. 6) thereof. Increasing the height of the surface feature 1134 may increase the range levels of the liquid within vessel in which the surface of the liquid contacts the face 1142. That is, in order to contact the physical surface feature 1134 the surface of the liquid need not be exactly aligned with the edge 1144, but can be positioned anywhere where it is in contact with face 1142, e.g. vertically between the edge 1144 and the corner 1143. This may allow a greater degree of flexibility for users as they need not match the liquid level exactly with the height of inner edge 1144 when filling the vessel 1100.

In the illustrated example, when the liquid 102 is at a level such that it contacts the first inner surface 1138, the interface angle 117 is the receding contact angle 116 between the liquid and the first inner surface 1138 (much like in the example of FIGS. 3 and 5). Alternatively, if the liquid 102 is at a level such that it contacts the inclined face 1142, the interface angle 117 is the sum of the contact angle between the liquid and the surface 1142 and the angle 1148 of the surface (a slope angle) relative to the reference plane 1119 (see FIGS. 4 and 6).

The slope angle 1148 may be between 0 and about 90 degrees, between about 45 and about 15 degrees, and in the illustrated example the slope angle 1148 is about 45 degrees. In this configuration, the meniscus may be generally flat (i.e. the interface angle 117 may be about 90 degrees) when the sum of the slope angle 1148 and the contact angle between the liquid and the angled face 1142 is about 90 degrees.

The effects of the inserts' surface topologies on the meniscus magnitude are summarized in Table 1. Use of an unfeatured insert resulted in a significant reduction of meniscus width 121 (as shown in FIGS. 1*a* and 1*c*) to about 50% compared to the untreated polystyrene culture wells surface. Of the step-like surface features 134, the flat step face 142, as shown in FIGS. 3 and 5, produced a 40% reduction of meniscus magnitude relative to the unfeatured insert control, and the sloped step face 1142 configuration, as shown in FIGS. 4 and 6, eliminated the observable meniscus (i.e. there was no observable meniscus created using the sloped step face 1142).

When the level of the liquid was increased above the step edges 144, 1144 of the surface features 134, 1134, a distinct liquid/solid interface and a background of even intensity was observable due to the opaque nature of the plastic inserts.

TABLE 1

Effect of inserts on meniscus magnitude, with the liquid level at the lower edge of the inserts.

| Insert | Meniscus Width (mm) |
|---|---|
| Untreated, no insert | 2.2 |
| Unfeatured insert | 1.2 |
| Flat-step insert | 0.7 |
| Sloped-step insert | 0.0 |

Optionally, the meniscus reducing members 132 and 1132 may also include a chemical treatment or coating type meniscus reducing member. For example a chemical treatment or coating type meniscus reducing compound can be applied to some or all of the physical surface features 134 and 1134 to help further modify the contact angle, and preferably to provide a desired receding contact angle. Optionally, the surface treatment and/or coating can be applied to the faces 138, 140 and surface 142 (and similarly faces 1138, 1140 and surface 1142). Alternatively, the surface treatment and/or coating material may only be provided on at least one of the faces 138, 140 and 142 (and like faces 1138, 1140 and 1142). For example, the application of coating material may be limited to step face 142 (1142), and/or the surface 142 (1142) and at least one of the first and second faces 138, 140 (1138, 1140).

Providing a chemical treatment and/or surface coating material on the surface feature 1134, including angled step face 1142, may help further reduce the meniscus formed between step face 1142 and the liquid. The combination of both the physical meniscus reduction and the chemical/surface coating type meniscus reduction may help the angled step face 1142 configuration provide the desired receding contact angle, while still preserving the flexibility with respect to the fill-level of the liquid within vessel 1100.

The effect of the surface coating material can be measured by comparing an uncoated contact angle to a coated contact angle. For the purposes of this application, an uncoated contact angle is the contact angle formed between a surface, for example the physical surface feature 134, 1134 and a given liquid in the absence of a coating material. It may be possible to determine an uncoated intrinsic contact angle and uncoated advancing and receding contact angles, as described herein. In contrast, the coated contact angle is understood to be the contact angle formed between the same surface and the same liquid after the surface has been coated with the coating material. It may be possible to determine coated intrinsic, advancing and receding contact angles.

Optionally, the combination of the surface, e.g. the physical surface feature 134, 1134, and the coating material to be selected so that the meniscus reducing member provides a coated intrinsic contact angle and a coated receding contact angle when contacted by the liquid, and the coated receding contact angle is between about 75 degrees and about 110 degrees and is closer to 90 degrees than the coated intrinsic contact angle.

Alternatively, the combination of the surface, e.g. the physical surface feature 134, 1134, and the coating material to be selected so that the meniscus reducing member provides a coated intrinsic contact angle and a coated receding contact angle when contacted by the liquid, and the coated receding contact angle is between about 90 degrees and less than 180 degrees, or between about 110 degrees and about 160 degrees, or between about 120 degrees and about 150 degrees and is farther from 90 degrees than the coated intrinsic contact angle.

The coating material can be applied to the vessel wall second inner surface 138 by any suitable method. Examples of suitable application methods include:

Application or insertion of pre-formed materials (with or without adhesive);

Application of the material using a physical applicator followed by removal of excess material;

Application by immersion of the vessel into the coating material or a solution thereof, followed by drying;

Application of a melted material followed by cooling and solidification;

Dissolution of the coating material in a suitable solvent and application of this solution, followed by removal of the solvent through evaporation, aspiration, and/or washing;

Application of a material that cures upon exposure to air, heat or light such as UV light; and Application of an agent following addition of the material that causes the material to cure.

Alternatively, the second inner surface 138, 1138 of the culture vessel could be made of the coating materials if the material being used is sufficiently rigid.

Any suitable physical applicator may be used to apply to coating material, including, for example, a lint-free material, such as a lint-free tissue, which may be used on its own or attached to a suitable applicator device.

After the coating material is applied, it may be allowed to set for a sufficient period of time, excess may be removed if necessary (for example using a clean physical applicator) and the material allowed to cure, for example by incubating for a suitable time and temperature. A person skilled in the art would be able to determine curing conditions based on the vessel type and identity of the coating material. For example polystyrene vessels may be incubated at a temperature of about 50° C. to 80° C., where PTFE vessels may be incubated at higher temperatures, for example about 150° C. to about 250° C. Vessels are cooled to room temperature prior to use.

The time between applying the coating material and using the vessel will depend on the application method. Vessels prepared with materials that are pre-formed can be used immediately. Vessels prepared with materials that require removal of a solvent or curing will require anywhere from a few minutes to several days depending on the material, the application method and the atmospheric conditions as would be known to a person skilled in the art.

A preferred coating material is any material that can be made to adhere to the physical surface features 134, 1134 (as an integral portion of a vessel and/or as a separate insert) to result in a dynamic minimum (receding) contact angle of about 90 degrees (or within any of the ranges recited herein) with common aqueous solutions and culture media. Potential coating materials include, without limitation, one or more of the following, or any suitable combination thereof:

liquid siliconizing agents such as solutions of methylsiloxanes, methylvinylsiloxanes, and methyl-perfluorobutylethylsiloxanes and their copolymers;

methyl perfluorobutylethyl siloxane, methylhydrogen siloxane, dimethyl siloxane, and methyl vinly siloxane, trimethylsiloxy-terminated methyl(perfluorobutylethyl) siloxane, and trimethylsiloxy-terminated methylhydrogen siloxane.

fluoropolymer agents, including fluoropolymer solutions in low boiling point fluorosolvents;

paraffin waxes;

polyolefin waxes;

animal and insect waxes, including beeswax, shellac, spermaceti, lanolin;

vegetable waxes, including bayberry, candelilla, carnauba, castor, esparto, Japan, jojoba oil, ouricury, and rice bran;

mineral waxes, including ceresin, montan, ozocerite, and peat;

wax-like saturated fatty acids, including lauric, myristic, palmitic, margaric, stearic, arachidic, behenic, tetracosanic, lignoceric, cerotic, and melissic acid;

non-wax-like saturated fatty acids, including butyric, caproic, caprylic, and capric acid;

wax-like unsaturated fatty acids, including tiglic, hypogaeic, gaidic, physetoleic, elaidic, isooleic, erudic, brassidic, and isoerudic acids;

non-wax-like unsaturated fatty acids, including oleic, linoleic, alpha-linoleic, arachidonic, eicosapentaenoic, docosahexaenoic, and erucic acids;

wax-like fatty alcohols, including 1-tetradecanol, 1-pentadecanol, 1-hexadecanol, 1-heptadecanol, 1-octadecanol, 1-nonadecanol, 1-eicosanol, 1-heneicosanol, 1-docosanol, 1-tricosanol, 1-tetracosanol, 1-pentacosanol, 1-hexacosanol, 1-heptacosanol, 1-octasanol, 1-nonacosanol, 1-tricontanol, 1-hentriacontanol, 1-dotriacontanol, 1-tritriacontanol, and 1-tetratriacontanol;

non-wax-like fatty alcohols, including 1-hexanol, 1-heptanol, 1-octanol, 1-nonanol, 1-decanol, 1-undecanol, 1-dodecanol, and 1-tridecanol;

solid materials, including materials comprising copolymers of hexafluoropropylene (HFP) and vinylidene fluoride (VDF or VF2), terpolymers of pertetrafluoroethylene (PTFE) or tetrafluoroethylene (TFE), vinylidene fluoride (VDF) and hexafluoropropylene (HFP) as well as perfluoromethylvinylether (PMVE), silicon (available commercially as Viton™ from Dupont Performance Elastomers); Buna Nitrile (also called standard grade nitrile), fluorosilicon, neoprene, urethane, HSN (Highly Saturated Nitrile), silicone rubbers, and ethylene propylene diene monomer (EPDM); and polyperfluoroalkyl and perfluoropolyether polymers, fluorourethane coatings, perfluoro-polyether and perfluoro-alkyl fluorosilanes Superhydrophobic particle suspension coatings such as FluoroPel and PFC M1104V from Cytonix (Beltsville, Md.), or rod or brush-based superhydrophobic coatings.

Suitable coatings may also include various esters of the above-listed fatty acids with any suitable fatty alcohols, or sterols such as cholesterol, and/or glycerols.

The inventors have discovered that one example of a coating material is the silicone based Dehesive® solution manufactured by Wacker which the inventors believe contains about at least 63% by weight of one or more of methyl perfluorobutylethyl siloxane, methylhydrogen siloxane, dimethyl siloxane and methyl vinly siloxane in solution which are crosslinked with a crosslinking solution that comprises at least about 60% by weight of one or more of trimethylsiloxy-terminated methyl(perfluorobutylethyl) siloxane, and trimethylsiloxy-terminated methylhydrogen siloxane.

Optionally, the coating material may be silicone based, fluoropolymer based, petroleum jelly, paraffin wax, EPDM or Buna Nitrile or is an insert that is made of silicone, EPDM or Buna Nitrile or that is coated with a coating material that is silicone based, fluoropolymer based, petroleum jelly, paraffin wax, EPDM or Buna Nitrile. Optionally, the silicone-based material may include non-crosslinked siloxane, methylsiloxane or methylvinyl siloxane or copolymers thereof.

The meniscus reducing members 132, 1132 and vessels and/or inserts containing members 132 and 1132 may be particularly useful when the vessel is used to contain viscous aqueous solutions or gels. By viscous it is meant that the solution has a viscosity or resistance to flow that is greater than the viscosity of water, or greater than about 1 mPa·s, suitable greater than about 5 mPa·s, and up to about 4000 mPA·s. Optionally, the viscous aqueous solution may be any such solution commonly used in cell culture or cell-based assays, for example, biological buffers and any medium that can support the growth of cells, including without limitation, Iscove's modified Eagle's Medium (IMDM), Dulbecco's modified Eagle's Medium (DMEM), Hank's balanced salt solution, methylcellulose-based media (such as MethoCult™), agar-based media, gelatine-based media and collagen-based media. Alternatively, the viscous aqueous solution may be a solution comprising biopolymers, such as proteins, glycoproteins, peptides, polysaccharides and/or oligonucleotides and/or water soluble polymers such as polyalkylene glycols. In yet another embodiment of the application, the solution is one that comprises molecules that alter the surface properties of the interior walls of the vessels, thereby altering the contact angle of the walls when the walls are wetted with the solution.

Preferably, the coating materials are applied to the physical surfaces features 134, 1134 in a manner and amount effective to reduce the curvature in the meniscus of cell culture medium or other common aqueous solutions by resulting in a surface energy to enable a receding contact angle of about 90 degrees, suitably about 75 degrees to about 110 degrees, more suitably about 80 degrees to about 110 degrees, even more suitably about 85 degrees to about 105 degrees and about 90 degrees. The particular coating material selected, the thickness of the coating, and other properties of the coating material may be chosen based on a variety of factors, including, for example, the geometry of the physical surface features 134, 1134.

Alternatively, the coating materials are applied to the physical surfaces features 134, 1134 in a manner and amount effective to reduce the curvature in the meniscus of cell culture medium or other common aqueous solutions by resulting in a surface energy to enable a receding contact angle of about 90 degrees to less than 180 degrees, suitably about 110 degrees to about 160 degrees, and more suitably to about 120 degrees to about 150 degrees. The particular coating material selected, the thickness of the coating, and other properties of the coating material may be chosen based on a variety of factors, including, for example, the geometry of the physical surface features 134, 1134.

Optionally, as illustrated in FIGS. 3 and 4, the meniscus reducing members 132 and 1132, including physical surface features 134 and 1134, may be integral with the vessels 100 and 1100 and the first and second portions 138, 140 and 1138 and 1140 and the step faces 142 and 1142 may be integral with, and form a portion of, the interior surfaces 105 and 1105 of the sidewalls 104 and 1104. Alternatively, as illustrated in FIGS. 5 and 6, the meniscus reducing members 132 and 1132 may be provided as separate insert members 146 and 1146, in this example an annular or ring-like insert members 146 and 1146, that are sized to fit within a complementary vessel so that the surface features 132 and 1132 overlie at least a portion of the vessel's interior surface and contacts the liquid.

The insert members 146 and 1146 may be made from any suitable material as described herein, and need not be the same material as the surrounding vessel. For example, a polymeric insert member may be received within a test tube, beaker, vial or other vessel. It is understood that the overall shape and dimensions of the insert members 146 and 1146 may be chosen based on the shape and size of a particular vessel.

Optionally, the physical surface features 134 and 1134 may extend generally continuously around the entire inner perimeter of the interior surfaces 105 and 1105 of their respective vessels 100, 1100. Alternatively, the physical surface features 134 and 1134 may extend only part way around the inner perimeter of the interior surfaces 105 and 1105. While the step faces 142 and 1142 are illustrated as being substantially planar, optionally the step faces 142 and 1142 may be curved or otherwise non-planar surfaces.

Suitable materials for constructing the step-like physical surface features 134 and 1134, either as an insert 146, 1146 or an integral portion of the vessels 100, 1100, may be any of the materials used to form the vessels 100, 1100 including, for example polystyrene, polypropylene, polycarbonate, polyvinylchloride polytetra-fluoroethylene (PTFE), silicone, EPDM (ethylene propylene-diene monomer), Buna Nitrile and ultra-high molecular weight (UHMW) plastic.

The vessels 100, 1100, and others utilizing the meniscus reducing members 132, 1132 described herein may be used for a variety of purposes, including for culturing cells or for performing imaging-based assays. Imaging-based assays may be any such assay used in both the biological and chemical arts, for example, colony forming cell (CFC) assays, gene sequencing, combinatorial chemistry, drug discovery and proteomics.

Optionally, the imaging of the cells or imaging-based assay of a liquid that is in contact with a suitable meniscus reducing member may be performed using visible light, ultraviolet light, infrared light and/or fluorescence, in particular visible light. Visible light imaging may be performed, for example, using darkfield mode, brightfield mode, phase contest or digital interference contrast. Optionally, the imaging may be done manually or automatically and/or the cells imaged may be in a cell colony.

The surface coating materials may be applied to the interior surfaces of the vessel and/or physical surface feature using a variety of suitable techniques. According to a first method for coating separate inserts (for example as illustrated in FIGS. 5 and 6) to be inserted into vessels a coating of a polymer of siloxane (Syl-off™ Q2-7785 (monomer), Syl-off™ Q2-7560 (cross-linker), Dow Corning) diluted in in a solvent was applied to the inserts. The solvent may be any suitable solvent that is compatible with the selected coating material and provides the desired viscosity for the coating process, including, for example, hexane and other hydrocarbon-based or organic solvents.

In this method the inserts are dipped into a container of the coating solution such as to completely cover the insert and are placed on a surface to allow excess coating to flow off. The inserts can be allowed to drain for any suitable period of time to allow a sufficient amount of the coating to flow off the insert, including, for example, between about 5 and about 30 minutes, or longer. The inserts are then placed into the wells of a 6-well plate and cured. The curing process can be conducted under any conditions that are appropriate for curing the selected coating material. For example, the inserts may be cured at an elevated temperature of between about 50° C. and about 100° C., and may be cured at about 70° C. The curing time may be any suitable time, and may be between about 1 hour and about 12 hours, and in some configurations may be at least 2 hours. Inserts coated with a cured surface coating may then be placed inside suitable vessels and exposed to the liquids therein.

According to a second method for coating the inserts, a number of inserts are stacked end to end in a tube with a diameter slightly larger than the inserts and then rotated around the tube's axis minutes while a desired amount of coating solution, for example is added to the tube. Optionally, the amount of coating solution added to the tube can be between about 250 uL and about 500 uL of solution per insert, and preferably is about 330 uL of solution per insert.

As the tube is rotated, the solution can coat the walls of each insert. The tube can be sized to hold any desired number of inserts, and optionally can be sized to hold about 15 inserts. The coating solution can be as kept inside the tube during rotation by capping the ends of the tube The tube can be rotated at any suitable speed that allows the coating material to coat the inserts therein. Optionally, the tube may be rotated between about 1 rpm and about 25 rpm or more, and preferably may be rotated at about 8 rpm. The tube can be rotated for any suitable time period, and preferably is rotated until at least some of the solvent mixed with the coating solution has evaporated. Optionally, the tube may be rotated for between about 5 minutes and about 30 minutes or longer, and optionally may be rotated for about 20 minutes to allow the hexane to evaporate. The coated inserts can then be placed into the wells of a 6-well plate one at a time. The whole plate is then cured at 70° C. for at least 2 hours, or under any other suitable curing conditions as described herein.

The solvent, for example hexane, is used to reduce the viscosity of the coating material (e.g. siloxane) so that it would flow down the insert wall as it was rotated within the tube. A coating material with lower viscosity may be able to flow sufficiently on its own, and may not require an additional solvent.

According to another method of coating an insert, an insert including a generally horizontal step face 142 surrounding the inner circumference of a suitable 35 mm well was generated by placement of an insert into the interior of the well. The insert may be made from any suitable material, including for example, a nitrile gasket giving a step face 142 width of 1 mm and a distance between the step face 142 and the well bottom 106 of 1 mm, and manufactured from a strip of PTFE sheeting giving a step face 142 width of about 1 mm and a distance between the step face 142 and the well bottom 106 of 0.5 mm. The inserts can be placed flush against the well bottom of the wells in a suitable well plate, such as a Greiner 607102 6-well plate. The interior wall surface of the well above the step feature, for example surfaces 138, 1138 described above can then be coated with any suitable coating material. Preferably, the coating material is either a hydrophobic or superhydrophobic material.

For example, a superhydrophobic coating material, such as, for example, WX2100 (Cytonix LLC, Md.), can be sprayed onto the inner surface of a polystyrene ring with a height of about 10 mm and thickness of about 0.5 mm (outer diameter ~35 mm). The coating can be allowed to dry for any suitable time (e.g. approximately 1 hr at room temperature) prior to placement into 35 mm wells containing the nitrile gasket described above. This assembly provides a superhydrophobic wall surface (3.g. 138, 1138) above a 0.5 mm step (e.g. the exposed nitrile gasket).

Alternatively, a hydrophobic overlying surface can be provided when 35 mm wells with the PTFE inserts are placed onto a rotator platform oriented about 1° to about 5° from vertical so that the plane of the well bottom was perpendicular to the axis of rotation. A coating solution, such as a 10% siloxane solution (Wacker Dehesive 920 and crosslinker V90) can be applied (e.g. about 250 uL per well) to the interior side wall while rotating the wells at a suitable speed (such as between about 1 rpm and about 25 rpm, and optionally about 8 rpm). Preferably, the siloxane solution is prevented from overflowing the insert and contacting the well bottom.

The wells can be rotated for any suitable time period to allow a sufficient quantity of the solvent in the coating solution to evaporate. For example, rotation can be continued for about 5 minutes or more to evaporate most of, or all of the solvent. The coating can then be cured using any suitable curing process, including those described herein.

In examples in which the physical surface feature is integrally formed with the vessel (for example as illustrated in FIGS. 3 and 4) the coating material can be applied directly to the interior surfaces of the vessels. According to one method, a well plate can be formed such that each well has a stepped interior surface (see FIG. 3 or 4). Optionally, the wells can include a vertical face (first surface 137) that is about 1.25 mm high and a horizontal step face 142 that is about 0.75 mm wide and followed the inside circumference of each well bottom.

The plates can be coated above the step face 142 with any suitable coating material, including, for example, a hydrophobic siloxane based coating (Dehesive™, Wacker, Germany) and a superhydrophobic nano-particle based coating (FluoroPel, Cytonix, USA). The siloxane-based coating can be prepared as a solvent-free solution of the siloxane monomer, crosslinker, and catalyst. The nanoparticle-based coating can be provided at a suitable concentration in a perfluoropolyether solvent by the manufacturer, and was used as supplied.

The coatings can be applied in any suitable method. Optionally, the coating can be applied according to one of the two methods described below, or in any other suitable method. Both of the methods described herein are intended to help reduce the chance of the coating material coming into contact with the well bottoms. In both methods the coating can be applied to a plate with the plate bottom oriented from vertical to about 5° from vertical and with the plate rotating in the plane of the plate bottom. It is preferable that the coating not get on the bottom of the wells since a hydrophobic well bottom may cause the fluid in the well to retract from the wall, causing a strong concave meniscus and reducing the total well bottom area covered. This in turn may result in optical interference for imaging the well.

In accordance with one coating application method, the coating material (e.g. a siloxane-based coating) can be diluted in hexane to a concentration suitable to reduce the viscosity to facilitate spreading over the well wall surface. The coating material is applied to the wall of each well while rotating at a rate of about 8 rpm (or any suitable rate between about 1 rpm and about 25 rpm or more). A suitable volume (for example about 200 uL) of coating material can be applied to each well over a suitable time period, including for example a period of between about ¼ to about ¾ rotation of the well. The coating material is preferably added to the lowest point on the horizontal well wall (e.g. step face 142) as it rotates. The viscosity of the coating and speed of rotation can be selected so that the volume of coating material would flow downward and disperse evenly over the surface 142 as it is rotated. This method may allow for evaporation of the solvent and may help provide an even coating around the circumference of the first surface 138, 1138 above the step 142, 1142 while helping to limit migration of the coating material onto the second surface 140, 1140 below the step face 142. The plates may be left to rotate for a suitable time period, such as, for example, about 5-30 minutes, to help remove residual solvent by evaporation. The plates can then be transferred to an oven to be cured under and suitable conditions, such as at about 70° C. for at least 2 hours for curing, to provide a solid hydrophobic or superhydrophobic film above the step surface 142 with little or no coating material below the step surface 142.

In accordance with another coating application a solvent-free formulation of a suitable coating material (such as siloxane/crosslinker/catalyst solution) is applied directly to the vessel wall by dispensing through any suitable apparatus, including, for example, a pipette tip attached to peristaltic pump with flexible tubing. As in the above method, the plate can be held in an orientation so that the plane of the plate bottom (e.g. plane 108, 1108) was approximately vertical (e.g. within about 0-5 degrees of vertical), and then rotated about an axis perpendicular to the plate bottom. The pipette tip can be aligned to dispense the coating at the lowest point on the well wall and offset about 2 mm from the horizontal step face (142). Dispensing of the coating solution can be conducted as the well is rotated about its rotational axis.

While the coating solution is being applied, the plate can be simultaneously moved away from the tip such that a continuous helical bead of coating solution with a suitable pitch (preferably a pitch of between about 1.5 to 2 mm) is applied to the vessel wall. The well may be rotated a suitable number of times during this process, for example between about 1 and about 10 times, and preferably about 4 times, to deposit between 12 and 60 uL (preferably between 20 and 25 uL) of coating material onto the vessel walls before the dispensing of the coating solution is stopped. The plate can then be placed in a generally horizontal orientation and the coating material may be allowed to settle for a desired time period, for example up to about 2 hours or more. During the settling period, the helical bead of coating solution can disperse into a continuous film over the well wall. The coating film may vary in thickness and may be thicker in the direction of the well bottom, with some coating material collecting on the step face (142). After settling, the coating can be cured as described herein.

Example 1: Measurement of Meniscus in Brightfield Images

Brightfield images of about 1 mL of fluid in 6-well plates were acquired using STEMvision™ (Stemcell Technologies Inc, Canada) following the recommended image acquisition procedure. This procedure includes a step to standardize illumination intensity and focal position. The dark area under the meniscus was measured using digital image processing methods. The % meniscus was then calculated as the dark area under the meniscus divided by the total well bottom area (excluding the step face).

Example 2—Coating a Cylindrical Insert

An insert for standard 6-well plates was custom manufactured of polystyrene. The insert was roughly cylindrical with a height of about 1 cm, a wall thickness of about 0.5 mm and an outside diameter that matched the inner diameter of a well in a standard 6-well plate. Some of the inserts were manufactured additionally with 3-5 posts spaced equidistantly around one end of the cylinder. These posts were about 1 mm high and served to keep the entire rim of the insert from touching the bottom of the well.

A coating of a polymer of siloxane (Syl-off™ Q2-7785 (monomer), Syl-off™ Q2-7560 (cross-linker), Dow Corning) was applied to the inserts. Coating solutions containing the Syl-off monomer (33%-99% w/w) and crosslinker (1%-67% w/w) were prepared and diluted in hexane to a viscosity suitable for uniform coating of the insert surfaces. Two methods were utilized to apply the coating to the inserts. In the first method the inserts were dipped into a container of the coating solution such as to completely cover the insert and then placed on a surface to allow excess coating to flow off for about 5 to 30 minutes. The inserts were then placed into the wells of a 6-well plate and cured at 70° C. for at least 2 hours. In the second method the inserts were stacked end to end in a tube with a diameter slightly larger than the inserts and then rotated around the tube's axis minutes while about 330 uL of solution per insert was added to the tube. As the tube rotated, the solution coated the walls of each insert. The tube was long enough to hold about 15 inserts. The solution was kept inside the tube during rotation by capping the ends of the tube. The tube rotated at about 8 rpm for 20 min to allow the hexane to evaporate. The inserts were then placed into the wells of a 6-well plate one at a time. The whole plate was then cured at 70° C. for at least 2 hours. The hexane was used to reduce the viscosity of the siloxane so that it would flow down the insert wall as it rotated. A siloxane with lower viscosity may not require a solvent.

Figure 7:
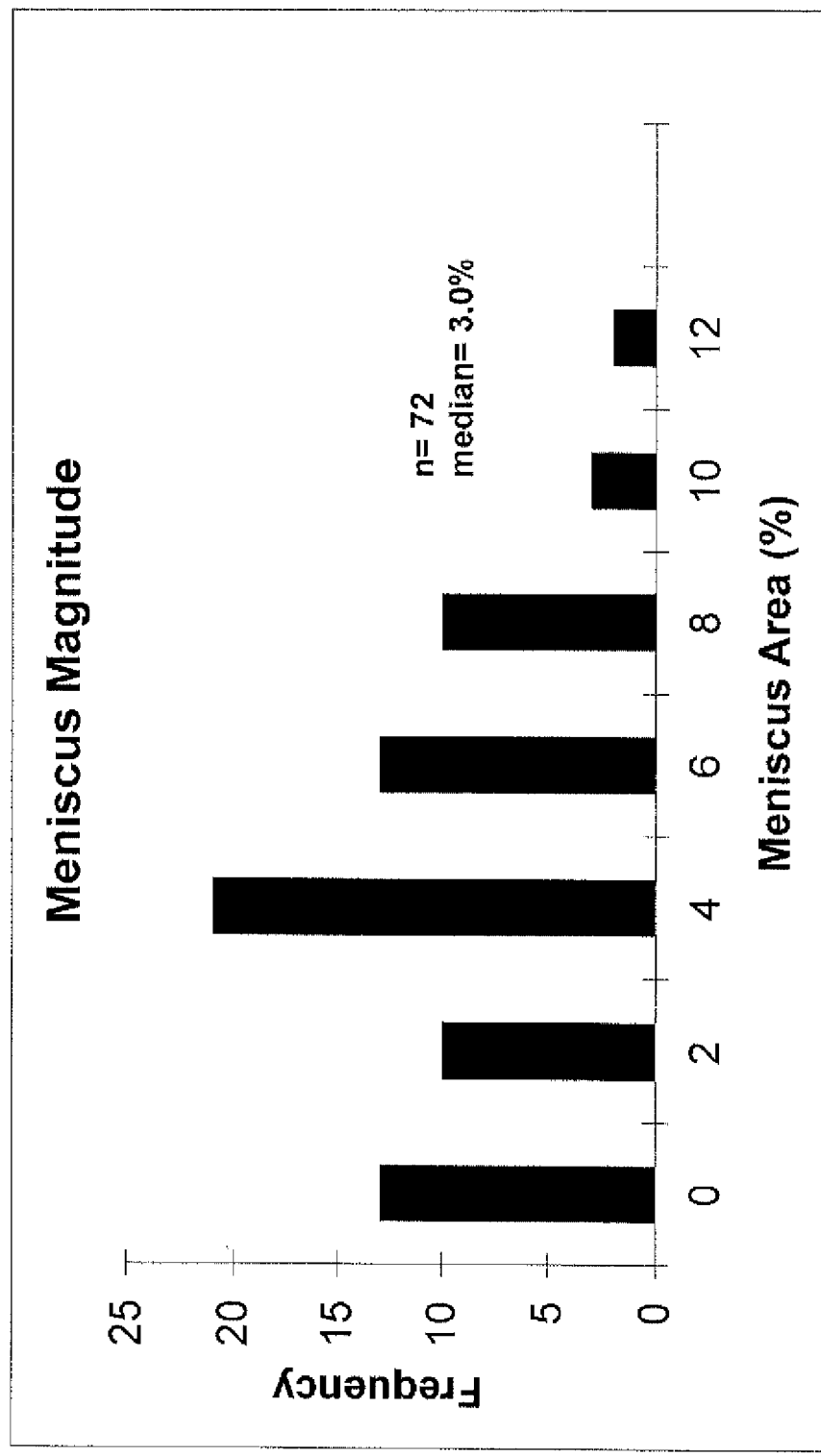
FIG. 7 is a graph showing the % meniscus coverage for wells in a 6-well plate that have an insert on the well wall coated with a coating material.

The wells with coated inserts gave excellent meniscus reduction in semi-solid media cell culture assay of hematopoietic progenitors. About 1 mL of Methocult™ (Stemcell Technologies, Canada) was added to each well and the plate placed in a humidified incubator for 7 days. The plates were then imaged and analyzed as described in Example 1. FIG. 7 shows the meniscus % coverage of the well for n=72 wells prepared following the second coating application method of this example. For comparison, the % meniscus in a standard, untreated 6-well polystyrene plate is 29%

Example 3—Coating a Stepped Insert

In this example, a step feature consisting of a horizontal step face 142 surrounding the inner circumference of a 35 mm well was generated by placement of an insert into the interior of the well. The inserts were either made from anitrile gasket giving a step face 142 width of 1 mm and a distance between the step face 142 and the well bottom 106 of 1 mm, or manufactured from a strip of PTFE sheeting giving a step face 142 width of about 1 mm and a distance between the step face 142 and the well bottom 106 of 0.5 mm. The inserts were placed flush against the well bottom of Greiner 607102 6-well plates. The interior wall surface above the step feature was coated with either a hydrophobic or superhydrophobic material.

Superhydrophobic overlying surface: WX2100 (Cytonix LLC, Md.) was sprayed onto the inner surface of a polystyrene ring with a height of 10 mm and thickness of 0.5 mm (outer diameter ~35 mm). The coating was allowed to dry for approximately 1 hour at room temperature prior to placement into 35 mm wells containing the nitrile gasket described above. This assembly constitutes a superhydrophobic wall surface above a 0.5 mm step (exposed nitrile gasket).

Hydrophobic overlying surface: 35 mm wells with the PTFE inserts were placed onto a rotator platform oriented about 1° to 5° from vertical so that the plane of the well bottom was perpendicular to the axis of rotation. A 10% siloxane solution (Wacker Dehesive 920 and crosslinker V90) was applied (about 250 uL per well) to the interior side wall while rotating at 8 RPM. The siloxane solution was not allowed to overflow the insert and contact the well bottom. Rotation was continued for 5 minutes to all evaporation of the solvent. The coating was then cured at 70° C. for about 2 hrs.

In order to evaluate meniscus mitigation, a volume (about 1 mL) of MethoCult™ sufficient to result in a liquid level even with the edge of the horizontal ledge feature was placed into the treated wells. The wells were rotated to spread media and overflow the step feature to contact the treated surface around the entire well perimeter. The wells were placed in a humidified incubator for 5 days. The plates were imaged and analyzed as described in Example 1 prior to and after incubation. The results, summarized in the table below, demonstrate a negligible meniscus area resulted with both the hydrophobic and superhydrophobic coating.

| | Meniscus magnitude (% of well area) | |
| --- | --- | --- |
| Incubation period (days) | Hydrophobic | Superhydrophobic |
| 0 | 1.1% | 0.4% |
| 5 | 0.7% | 0.6% |

Example 4—Application of Coating to Stepped Plate

A 6-well plate with integral steps in each well as in FIG. 3 was custom manufactured of polystyrene. The step had a vertical face (first surface 137) that was 1.25 mm high and a horizontal step face 142 that was 0.75 mm deep and followed the inside circumference of each well bottom.

The plates were then coated above the step face with either a hydrophobic siloxane based coating (Dehesive™, Wacker, Germany) or a superhydrophobic nano-particle based coating (FluoroPel, Cytonix, USA). The siloxane-based coating was prepared as a solvent-free solution of the siloxane monomer (90-99% w/w), crosslinker (0.5%-10% w/w), and catalyst (1%-4% w/w). The nanoparticle-based coating was provided at a suitable concentration in a perfluoropolyether solvent by the manufacturer, and was used as supplied.

The coatings were applied in one of two ways, both of which were intended to minimize the chance of the coating coming into contact with the well bottoms. In both methods the coating was applied to a plate with the plate bottom oriented about 1° to 5° from vertical and the plate rotating in the plane of the plate bottom. It is preferable that the coating not get on the bottom of the wells since a hydrophobic well bottom may cause the fluid in the well to retract from the wall, causing a strong concave meniscus and reducing the total well bottom area covered. This in turn results in optical interference for imaging the well.

For first coating application method, the siloxane-based coating was diluted in hexane to a concentration suitable to reduce the viscosity to facilitate spreading over the well wall surface. The coatings were applied with a manual pipette to the wall of each well while rotating at a rate of 8 RPM. A volume of about 200 uL of coating was applied to each well over a period of about ¼ to ¾ rotation of the well. The coating is added to the lowest point on the horizontal well wall. The viscosity of the coating and speed of rotation were set such that the volume of coating would flow downward and disperse evenly over the wall as it rotated. This method allowed for evaporation of the solvent to provide an even coating around the circumference of the wall above the step while preventing migration of the coating below the step face. The plates were left to rotate for 5-30 minutes for removal of residual solvent by evaporation, leaving an even coating around the wall of the well above the step. The plates were then transferred to a 70° C. oven for at least 2 hours for curing, resulting in a solid hydrophobic or superhydrophobic film above the step surface with no coating below the step surface.

A second coating application method was evaluated for the siloxane-based hydrophobic coating. In this method, a solvent-free formulation of the siloxane/crosslinker/catalyst solution was applied directly to the well wall by dispensing through a pipette tip attached to peristaltic pump with flexible tubing. As in the above method, the plate was held in an orientation so that the plane of the plate bottom was approximately vertical, and then rotated about an axis perpendicular to the plate bottom. The pipette tip was aligned to dispense the coating at the lowest point on the well wall and offset about 2 mm from the horizontal step face (142). Dispensing of the coating solution began as the well rotated about its axis. The plate was simultaneously retracted from the tip such that a continuous helical bead with a pitch of 1.5 to 2 mm of the coating was applied. The well rotated about 4 times to deposit between 12 and 60 uL of coating material before dispensing of the coating solution was stopped. The plate was then placed on a table in a horizontal orientation and the coating allowed to settle for up to 2 hours. This resulted in the dispersal of the helical bead of coating solution to a continuous film over the well wall that thickened in the direction of the well bottom, with some coating collecting on the top face (142) of the step. The thickness of the coating was assessed qualitatively by eye. This qualitative assessment was assisted by addition of the blue dye Holcosil LSR Blue to the coating material (Holland Colours, Va.). A coating volume of about 20 to 25 uL resulted in the most uniform coating without causing the coating to overflow the step face (142). After settling, the coating was cured in an oven at 70° C. for at least 2 hours.

The stepped-well plates coated with both hydrophobic and superhydrophobic materials, and with either of the two methods (for the case of the hydrophobic siloxane coating) gave excellent meniscus reduction using semi-solid cell culture media. About 1 mL of Methocult™ (Stemcell Technologies, Canada) was added to each well and the plate placed in a humidified incubator for 7 to 12 days. The plates were then imaged and analyzed as described in Example 1.

For the first coating application method, the meniscus magnitude as a percentage of well area was about 0% for both the Cytonix and Dehesive coating materials after both 7 and 12 days in the incubator, whereas the siloxane coated control wells lacking a step feature showed a % meniscus area of 3% after incubation. In addition control stepped-wells with no coating showed a % meniscus area of 29% after incubation. Thus, the coating in combination with the step feature resulted in better meniscus reduction than the step feature alone. The coating in combination with the step feature also resulted in better meniscus reduction than the coating alone (as shown in FIG. 7).

Figure 8:
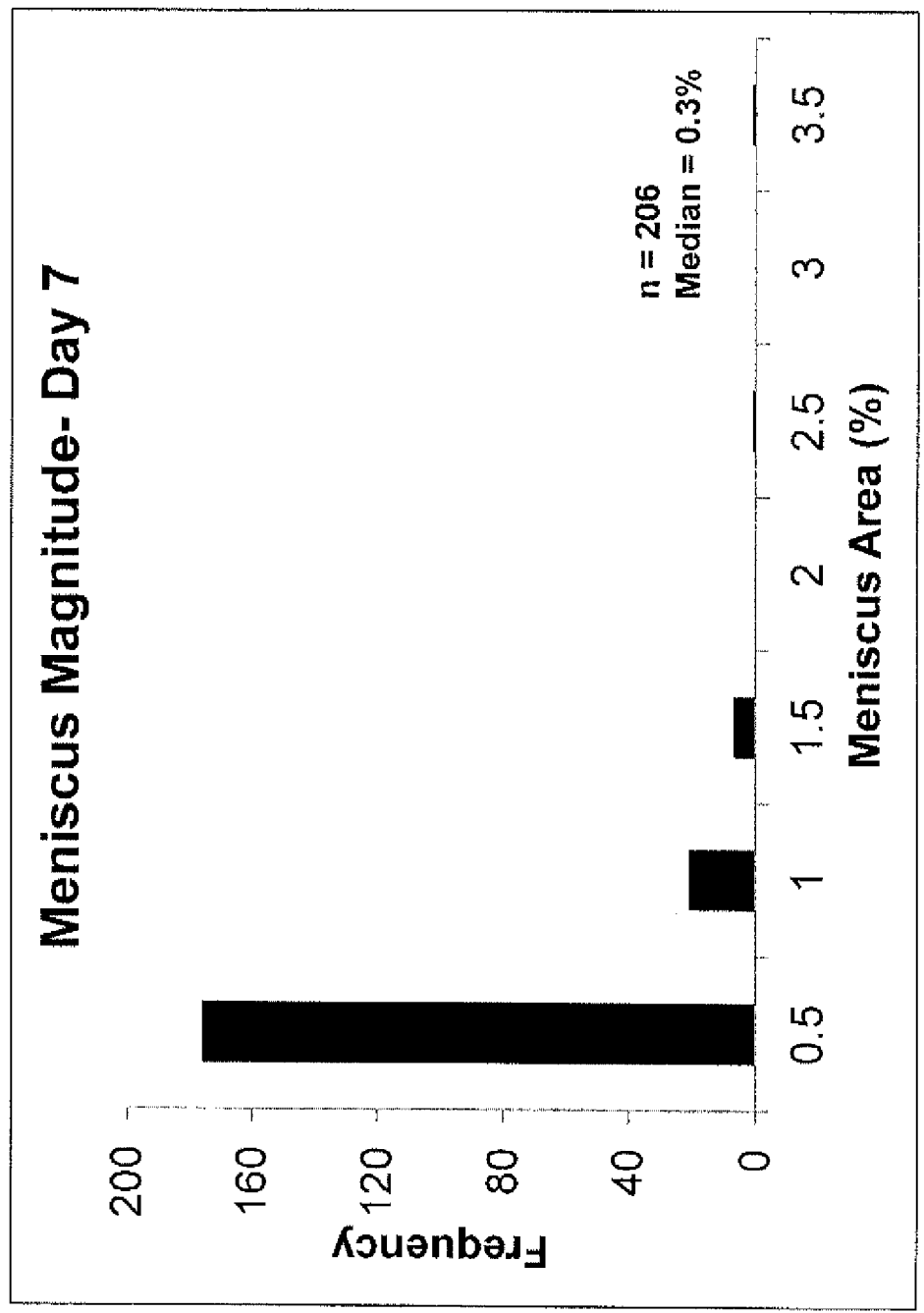
FIG. 8 is a graph showing the % meniscus coverage for wells in a 6-well plate with an integral step feature and coated with a coating material above the step.

FIG. 8 shows the meniscus magnitude as a % coverage of the well for n=206 wells prepared following the second coating application method of this example. The median % meniscus area was 0.3%. Again, the coating applied using the second application method, in combination with the step feature resulted in better meniscus reduction than the step feature alone and the coating alone. These results indicate that both the coating and the step feature may cooperate to give complete meniscus reduction.

What has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

We claim:

1. A vessel comprising:
   a) a closed bottom wall and a sidewall extending from the bottom wall to an open top portion for retaining a volume of liquid within the vessel, the sidewall comprising an interior surface;
   b) a physical surface feature overlying at least a portion of the interior surface to engage a free surface of a liquid in the vessel, the physical surface feature including a first inner surface, a second inner surface below the first inner surface when the liquid is contained in the vessel, and a third surface extending between the first and second surfaces, the third surface intersecting both the first and second inner surfaces, the first inner surface, second inner surface and third surface configured to physically alter a receding contact angle between the liquid and the physical surface feature;
   c) a step edge defined by the intersection of the second inner surface and the third inner surface, the step edge configured to engage the free surface of the liquid in the vessel; and
   d) a hydrophobic or superhydrophobic coating material applied to the first inner surface, wherein the second inner surface is substantially free from the coating material, and whereby the receding contact angle formed between the liquid and the first inner surface of the physical surface feature is between about 90 degrees and less than 180 degrees.

2. The vessel of claim 1, wherein the physical surface feature is disposed on a separate insert member configured to be received within the vessel.

3. The vessel of claim 1, wherein the receding contact angle formed between the liquid and the first inner surface of the physical surface feature is closer to 180 degrees than a receding contact angle formed between the liquid and the physical surface feature in the absence of the coating material.

4. The vessel of claim 1, wherein the receding contact angle formed between the liquid and the first inner surface of the physical surface feature is closer to 180 degrees than an unaltered receding contact angle measured between the liquid and a portion of the interior surface of the vessel.

5. The vessel of claim 1, wherein the coating material comprises at least one of i) a solution containing at least 63% by weight of one or more of methyl perfluorobutylethyl siloxane, methylhydrogen siloxane, dimethyl siloxane and methyl vinyl siloxane crosslinked with a crosslinking solution that comprises at least 60% by weight of one or more of trimethylsiloxy-terminated methyl(perfluorobutylethyl) siloxane, and trimethylsiloxy-terminated methylhydrogen siloxane, or at least one of ii) a coating of a polymer of siloxane, a siloxane based coating, a perfluorocarbon based coating and a nano-particle based coating.

6. The vessel of claim 1, wherein the physical surface feature is integral with the sidewall of the vessel.

7. The vessel of claim 1, wherein the physical surface feature extends continuously around an inner perimeter of the vessel.

8. The vessel of claim 1, wherein the receding contact angle formed between the liquid and the first inner surface of the physical surface feature is between about 110 degrees and about 160 degrees.

9. The vessel of claim 8, wherein the receding contact angle formed between the liquid and the first inner surface of the physical surface feature is between about 120 degrees and about 150 degrees.

10. The vessel of claim 1, wherein the coating material is superhydrophobic.

11. The vessel of claim 1, wherein the receding contact angle formed between the liquid and the first inner surface of the physical surface feature is closer to 180 degrees than an intrinsic contact angle formed between the liquid and the physical surface feature.

12. The vessel of claim 1, wherein the third surface is generally perpendicular to both the first and second inner surfaces or is inclined at an oblique angle to both the first and second inner surfaces.

13. The vessel of claim 1, wherein the second inner surface is laterally inwardly offset from the first inner surface.

14. The vessel of claim 1, wherein the third surface is curved.

15. The vessel of claim 1, wherein when the liquid is in the vessel the free surface is pinned at a level of the step edge.

* * * * *